US011559370B2

(12) United States Patent
Yanuma

(10) Patent No.: US 11,559,370 B2
(45) Date of Patent: Jan. 24, 2023

(54) ENDOSCOPIC TREATMENT TOOL

(71) Applicant: OLYMPUS CORPORATION, Hachioji (JP)

(72) Inventor: Yutaka Yanuma, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 1141 days.

(21) Appl. No.: 16/157,871

(22) Filed: Oct. 11, 2018

(65) Prior Publication Data
US 2019/0038376 A1 Feb. 7, 2019

Related U.S. Application Data

(63) Continuation of application No. PCT/JP2016/062617, filed on Apr. 21, 2016.

(51) Int. Cl.
*A61B 90/00* (2016.01)
*A61B 17/32* (2006.01)
(Continued)

(52) U.S. Cl.
CPC .......... *A61B 90/08* (2016.02); *A61B 1/00163* (2013.01); *A61B 1/273* (2013.01);
(Continued)

(58) Field of Classification Search
CPC ............. A61B 1/00163; A61B 1/273; A61B 17/00234; A61B 17/221; A61B 17/2909;
(Continued)

(56) References Cited

U.S. PATENT DOCUMENTS

2005/0143770 A1 6/2005 Carter et al.
2005/0272975 A1* 12/2005 McWeeney .......... A61B 1/0607
600/172
(Continued)

FOREIGN PATENT DOCUMENTS

JP H05-004806 Y2 2/1993
JP H07-299078 A 11/1995
(Continued)

OTHER PUBLICATIONS

Aug. 17, 2020 Office Action issued in Chinese Patent Application No. 201680084694.9.
(Continued)

*Primary Examiner* — Mohamed G Gabr
(74) *Attorney, Agent, or Firm* — Oliff PLC

(57) ABSTRACT

An endoscopic treatment tool, includes an elongated member having a distal end and a proximal end; a braid disposed between the distal end and the proximal end of the elongated member; a distal indicator disposed on the elongated member between a distal end and a proximal end of the braid, the distal indicator extending along a longitudinal axis of the elongated member; a proximal indicator disposed between the distal end and the proximal end of the braid on the elongated member at a more proximal side of the elongated member than the distal indicator, the proximal indicator extending along the longitudinal axis; and a pre-curved shape portion formed in a curved shape, wherein each of the distal indicator and the proximal indicator has a width less than half of an outer circumferential surface of the elongated member in a circumferential direction of the elongated member, respectively.

13 Claims, 17 Drawing Sheets

(51) Int. Cl.
  *A61B 1/00* (2006.01)
  *A61B 1/273* (2006.01)
  *A61B 17/00* (2006.01)
  *A61B 17/29* (2006.01)
  *A61B 18/14* (2006.01)
  *A61B 18/00* (2006.01)
  *A61M 5/00* (2006.01)
  *A61M 25/09* (2006.01)

(52) U.S. Cl.
  CPC .... *A61B 17/00234* (2013.01); *A61B 17/2909* (2013.01); *A61B 17/32* (2013.01); *A61B 17/320016* (2013.01); *A61B 18/1482* (2013.01); *A61B 2017/00818* (2013.01); *A61B 2018/00494* (2013.01); *A61B 2018/00601* (2013.01); *A61B 2090/0811* (2016.02); *A61M 5/007* (2013.01); *A61M 25/09* (2013.01)

(58) Field of Classification Search
  CPC ............ A61B 17/32; A61B 17/320016; A61B 18/1482; A61B 18/1492; A61B 2017/00818; A61B 2017/2212; A61B 2018/00494; A61B 2018/00601; A61B 2018/144; A61B 2090/0807; A61B 2090/0811; A61B 2090/376; A61B 2090/3937; A61B 90/08; A61M 25/09; A61M 5/007
  See application file for complete search history.

(56) References Cited

U.S. PATENT DOCUMENTS

| | | | |
|---|---|---|---|
| 2008/0051626 | A1* | 2/2008 | Sato ................... A61B 1/00179 600/101 |
| 2009/0048487 | A1 | 2/2009 | Yanuma |
| 2010/0010293 | A1* | 1/2010 | Sato ....................... A61B 1/018 600/101 |
| 2016/0361088 | A1* | 12/2016 | Maguire ............ A61B 17/3415 |

FOREIGN PATENT DOCUMENTS

| | | |
|---|---|---|
| JP | 2001-224554 A | 8/2001 |
| JP | 2007-301360 A | 11/2007 |
| JP | 2007-533400 A | 11/2007 |
| JP | 2009-045451 A | 3/2009 |
| JP | 2013-034652 A | 2/2013 |
| WO | 2005/107842 A1 | 11/2005 |
| WO | 2014/100397 A1 | 6/2014 |

OTHER PUBLICATIONS

Jul. 26, 2016 Search Report issued in International Patent Application No. PCT/JP2016//062617.

Oct. 24, 2017 Office Action issued in Japanese Patent Application No. 2017-537322.

\* cited by examiner

ENDOSCOPIC TREATMENT TOOL

This application is a continuation application based on a PCT International Application No. PCT/2016/062617, filed on Apr. 21, 2016. The content of the PCT International Application is incorporated herein by reference.

BACKGROUND OF THE INVENTION

Field of the Invention

The present invention relates to an endoscopic treatment tool.

Description of Related Art

Conventionally, procedures of cholangiopancreatography by inserting a catheter into the biliary and pancreatic ducts are known. The catheter used during such procedures is inserted into the biliary and pancreatic ducts, while being observed by an endoscope, from the duodenum through the duodenal papilla of a patient.

For example, in Japanese Examined Utility Model Application, Second Publication No. H5-004806, it is disclosed to attach a shape memory member to the distal portion of the tube in an endoscopic treatment tool having a tube that is inserted into the biliary and pancreatic ducts via the duodenal papilla, wherein the shape memory member is bendable toward a specific direction when the temperature becomes higher than a body temperature.

In the case of inserting the endoscopic treatment tool such as the catheter into the biliary and pancreatic ducts while being observed by an endoscope, the endoscopic treatment tool is inserted into the biliary and pancreatic ducts from the duodenal papilla while observing the duodenal papilla by the endoscope. At this time, a part of the endoscopic treatment tool inserted into the biliary and pancreatic ducts cannot be visually confirmed by the endoscope. Accordingly, a position and an orientation of the part inserted into the biliary and pancreatic ducts is confirmed using an X-ray image.

SUMMARY OF THE INVENTION

According to a first aspect of the present invention, an endoscopic treatment tool includes an elongated member having a distal end and a proximal end; a braid disposed between the distal end and the proximal end of the elongated member; a distal indicator disposed on the elongated member between a distal end and a proximal end of the braid, the distal indicator extending along a longitudinal axis of the elongated member; a proximal indicator disposed between the distal end and the proximal end of the braid on the elongated member, the proximal indicator disposed at a more proximal side of the elongated member than the distal indicator, and the proximal indicator extending along the longitudinal axis; and a pre-curved shape portion formed in a curved shape between a distal end of the distal indicator and the distal end of the elongated member, wherein each of the distal indicator and the proximal indicator has a width less than half of an outer circumferential surface of the elongated member in a circumferential direction of the elongated member, respectively.

According to a second aspect of the present invention, in the endoscopic treatment tool according to the first aspect, the distal indicator may be disposed between a position of 5 centimeters from the distal end of the elongated member toward the proximal end side of the elongated member and a position of 10 centimeters from the distal end of the elongated member toward the proximal end side of the elongated member, and the proximal indicator may be disposed between a position of 10 centimeters from the distal end of the elongated member toward the proximal end side of the elongated member and a position of 15 centimeters from the distal end of the elongated member toward the proximal end side of the elongated member.

According to a third aspect of the present invention, in the endoscopic treatment tool according to the first aspect, the distal indicator may have a first distal indicator and a second distal indicator, and the first distal indicator may be disposed at an opposite side with respect to the second distal indicator in a radial direction of the elongated member.

According to a fourth aspect of the present invention, in the endoscopic treatment tool according to the first aspect, the proximal indicator may have a first proximal indicator and a second proximal indicator, and the first proximal indicator may be disposed at an opposite side with respect to the second proximal indicator in a radial direction of the elongated member.

According to a fifth aspect of the present invention, an endoscopic treatment tool used with an endoscope having an observation optical system, the endoscopic treatment tool includes an elongated member having a distal end and a proximal end; a distal indicator disposed on the elongated member, the distal indicator extending along a longitudinal axis of the elongated member; and a proximal indicator disposed on the elongated member at a more proximal side of the elongated member than the distal indicator, the proximal indicator extending along the longitudinal axis, wherein the distal indicator is on a first part of the elongated member protruded from the endoscope by a first protrusion amount, the first part of the elongated member configured to be arranged within a field of view of the observation optical system, wherein the proximal indicator is on a second part of the elongated member protruded from the endoscope by a second protrusion amount larger than the first protrusion amount, the second part of the elongated member configured to be arranged within a field of view of the observation optical system, and wherein each of the distal indicator and the proximal indicator has a width less than half of an outer circumferential surface of the elongated member in a circumferential direction of the elongated member, respectively.

According to a sixth aspect of the present invention, in the endoscopic treatment tool according to the fifth aspect, the distal indicator may be disposed between a position of 5 centimeters from the distal end of the elongated member toward the proximal end side of the elongated member and a position of 10 centimeters from the distal end of the elongated member toward the proximal end side of the elongated member, and the proximal indicator may be disposed between a position of 10 centimeters from the distal end of the elongated member toward the proximal end side of the elongated member and a position of 15 centimeters from the distal end of the elongated member toward the proximal end side of the elongated member.

According to a seventh aspect of the present invention, in the endoscopic treatment tool according to the fifth aspect, the endoscope further having a channel for inserting a treatment tool, and a raising stand for raising the treatment tool inserted into the channel, the endoscopic treatment tool may further comprise a braid disposed between the distal end and the proximal end of the elongated member, and in a state in which the proximal indicator is positioned in the field of view of the observation optical system, a proximal end of the braid may be positioned at a more proximal side of the elongated member than a proximal end of the raising stand.

According to an eighth aspect of the present invention, in the endoscopic treatment tool according to the fifth aspect, the elongated member may have a pre-curved shape portion disposed between a distal end of the distal indicator and the distal end of the elongated member, the pre-curved shape portion having a restoring force so as to restore to a curved shape in which the longitudinal axis of the elongated member is curved, and a distal end of the distal indicator may be disposed in the vicinity of a proximal end of the pre-curved shape portion.

According to a ninth aspect of the present invention, in the endoscopic treatment tool according to the fifth aspect, a distal portion of the elongated member may have a pre-curved shape portion configured to restore to a curved shape, and a distal end of the pre-curved shape portion may be positioned in a range of the width of the distal indicator and the proximal indicator when viewed in a front view from a direction along the longitudinal axis.

According to an eleventh aspect of the present invention, in the endoscopic treatment tool according to the fifth aspect, the distal indicator may have a first distal indicator and a second distal indicator, and the first distal indicator may be disposed at an opposite side with respect to the second distal indicator in a radial direction of the elongated member.

According to a twelfth aspect of the present invention, in the endoscopic treatment tool according to the fifth aspect, the proximal indicator may have a first proximal indicator and a second proximal indicator, and the first proximal indicator may be disposed at an opposite side with respect to the second proximal indicator in the radial direction of the elongated member.

According to a thirteenth aspect of the present invention, in the endoscopic treatment tool according to the eleventh aspect, a color of the first distal indicator and the second distal indicator may be formed by a colored paint.

According to a fourteenth aspect of the present invention, in the endoscopic treatment tool according to the thirteenth aspect, the color of the first distal indicator may be different from the color of the second distal indicator.

According to a fifteenth aspect of the present invention, in the endoscopic treatment tool according to the twelfth aspect, a color of the first proximal indicator and the second proximal indicator may be formed by a colored paint.

According to a sixteenth aspect of the present invention, in the endoscopic treatment tool according to the fifteenth aspect, the color of the first proximal indicator may be different from the color of the second proximal indicator.

According to a seventeenth aspect of the present invention, a method of inserting an endoscopic treatment tool into the bile duct, includes inserting an elongated member of the endoscopic treatment tool into a channel of an endoscope, and protruding a distal end of the elongated member from a distal opening of the channel; inserting the distal end of the elongated member into the duodenal papilla; bringing the distal end of the elongated member to a branching region of the common bile duct and the cystic duct; recognizing an orientation of the distal end of the elongated member by observing a distal indicator disposed on the elongated member which is protruded from the duodenal papilla into the duodenal, when the distal end of the elongated member reaches the branching region of the common bile duct and the cystic duct; forwarding the elongated member toward the intrahepatic bile ducts; and recognizing the orientation of the distal end of the elongated member by observing a proximal indicator disposed on the elongated member which is protruded from the duodenal papilla into the duodenal, when the distal end of the elongated member reaches a branching region of the left hepatic duct and the right hepatic duct.

DETAILED DESCRIPTION OF THE INVENTION

First Embodiment

Figure 1:
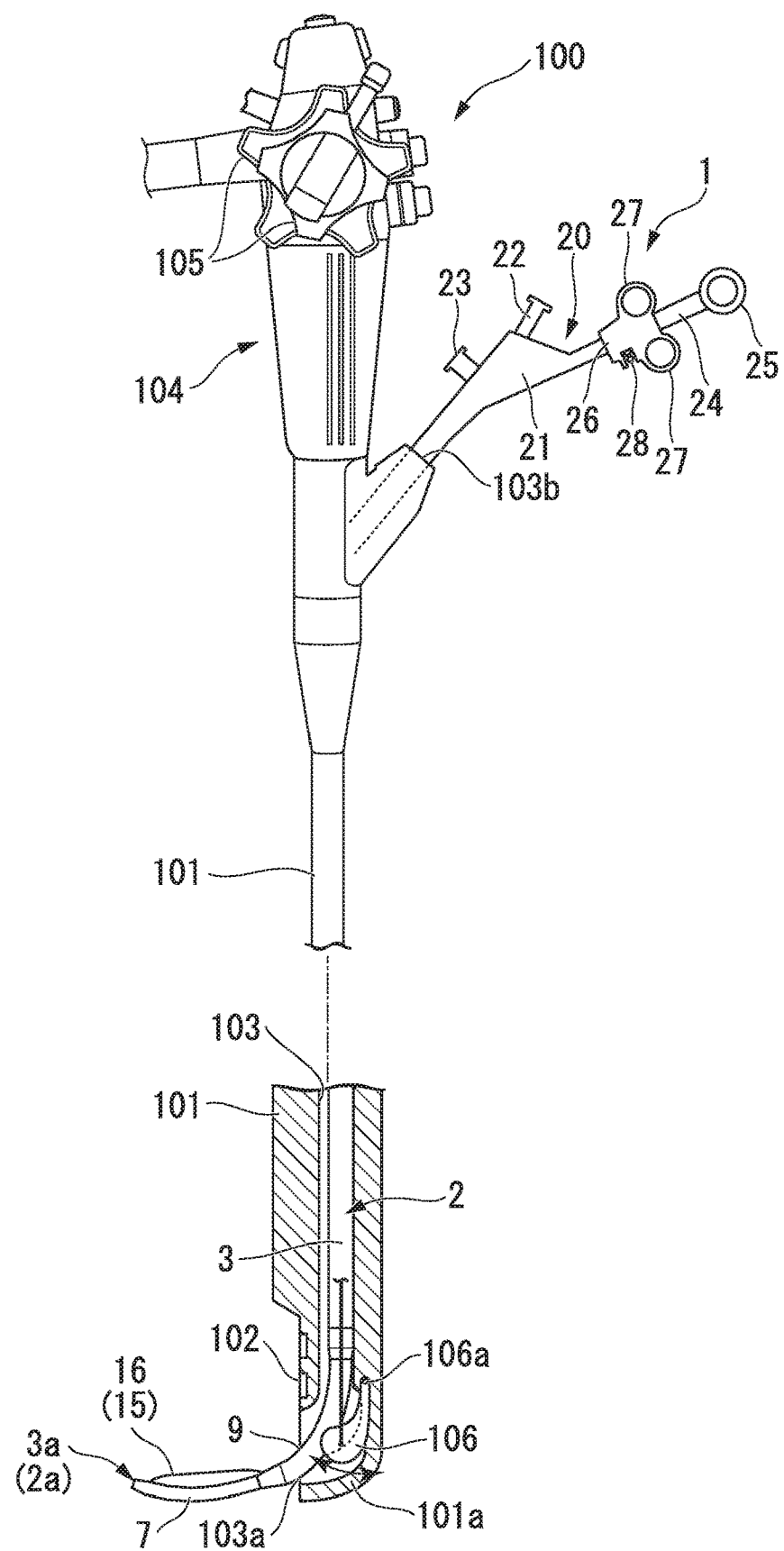
FIG. 1 is an overall view showing a state when an endoscopic treatment tool according to a first embodiment of the present invention is attached to an endoscope.
Figure 2:
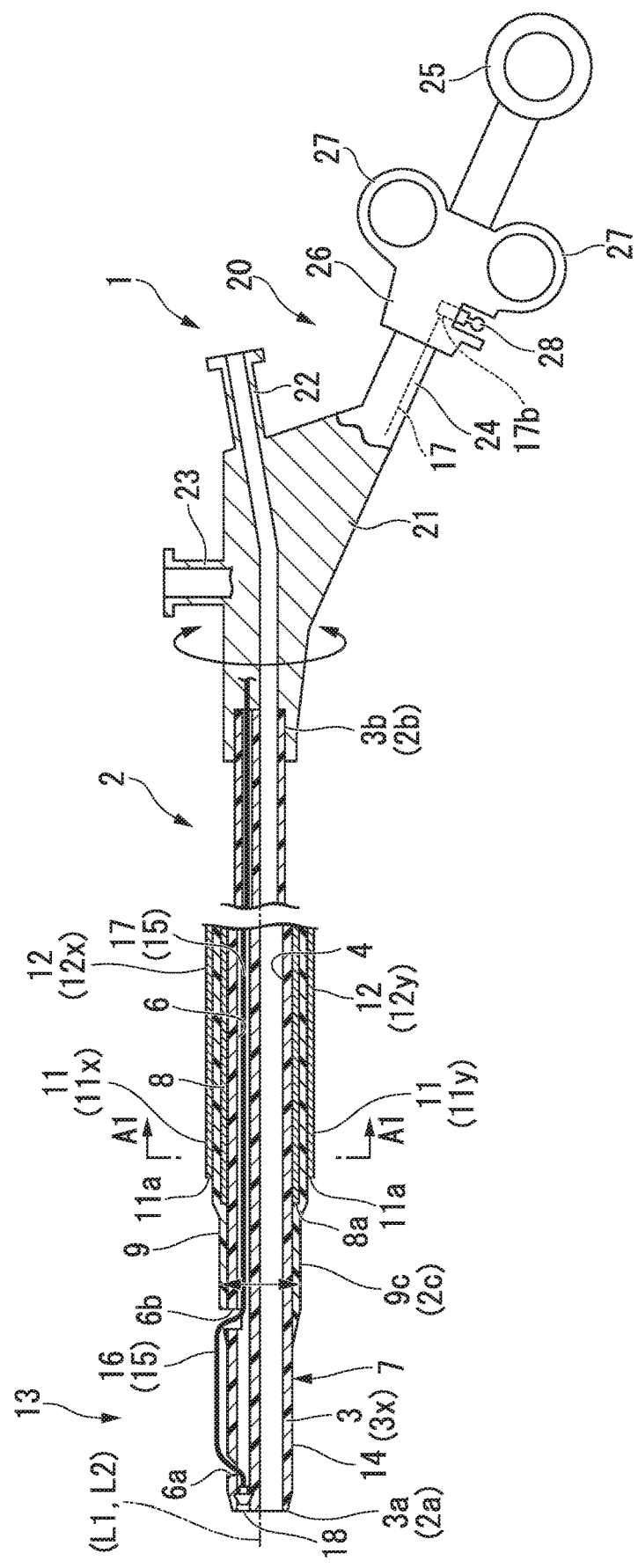
FIG. 2 is a sideview showing a partial cross section of the endoscopic treatment tool.
Figure 3:
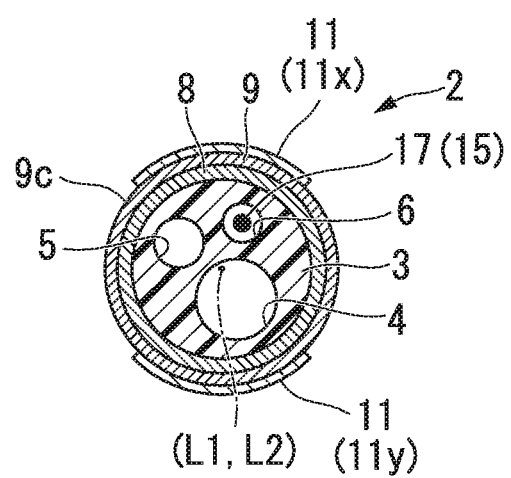
FIG. 3 is a view showing a cross section taken along A1-A1 line in FIG. 2.
Figure 4:
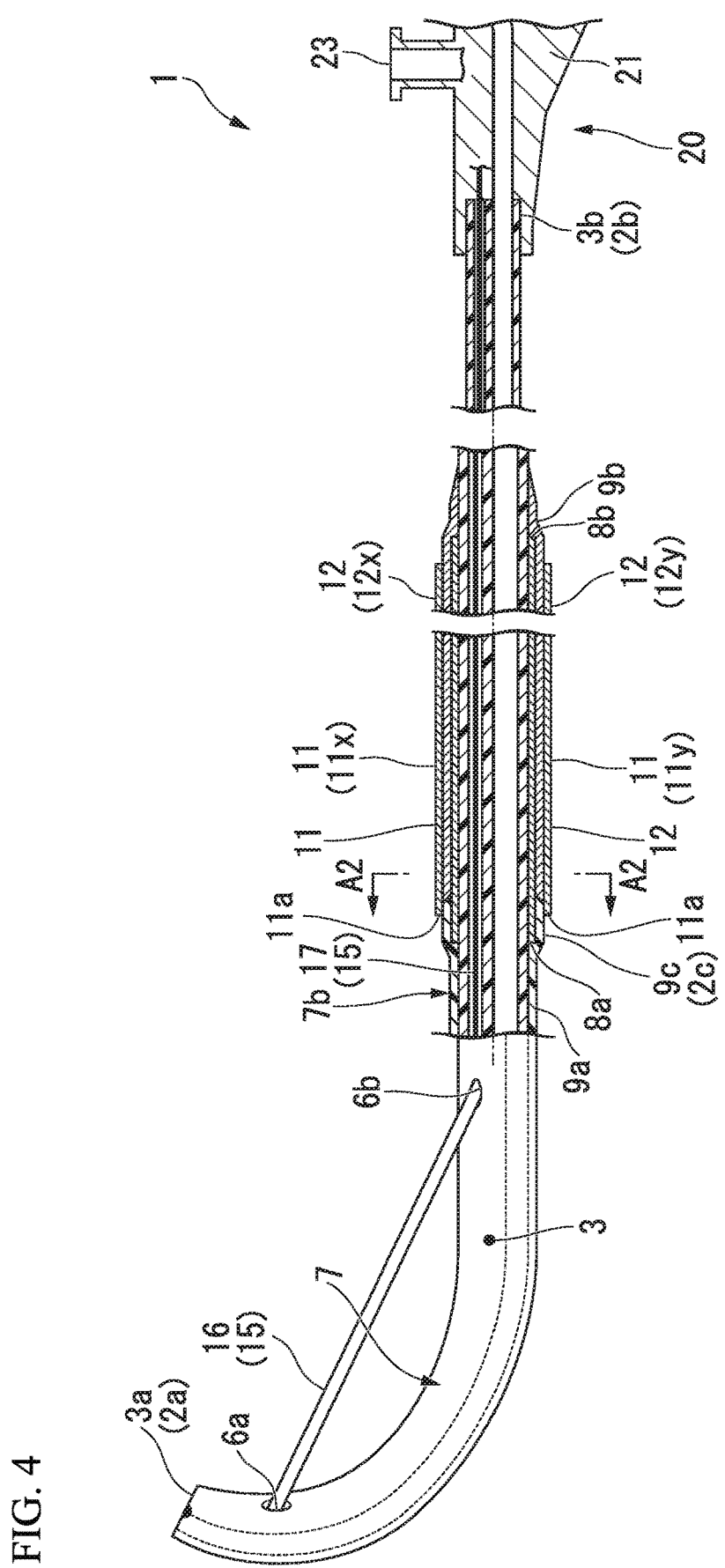
FIG. 4 is a sideview showing a partial cross section of a pre-curved shape portion of the endoscopic treatment tool when the pre-curved shape portion is in a curved state.
Figure 5:
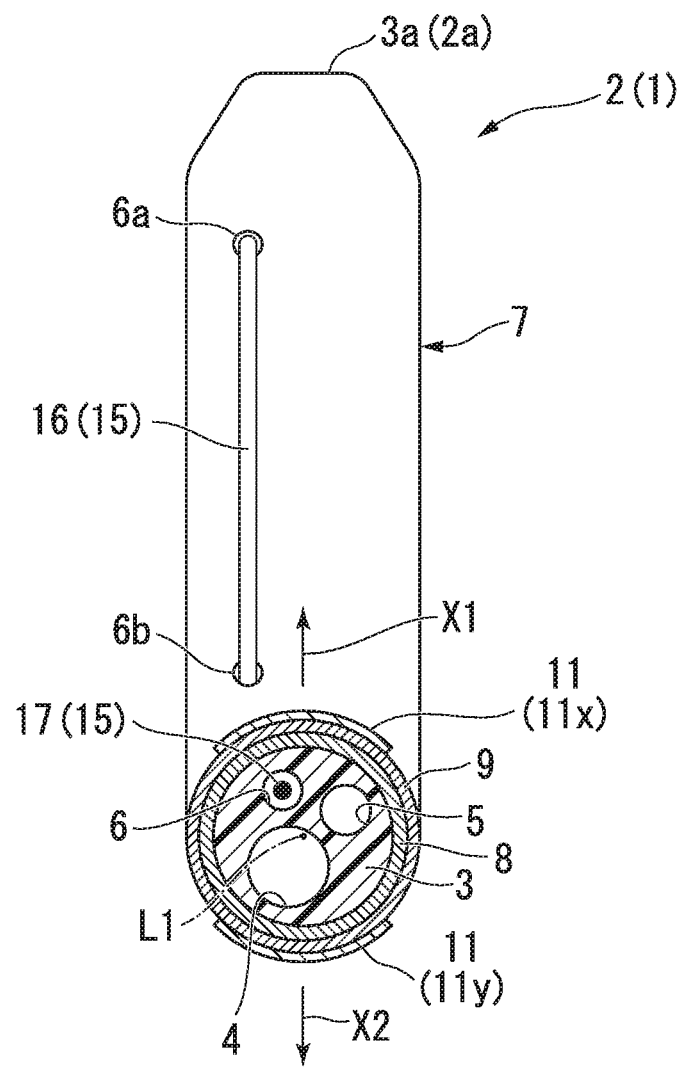
FIG. 5 is a view showing a cross section taken along A2-A2 line in FIG. 4.

A first embodiment of the present invention will be described. FIG. 1 is an overall view showing a state when an endoscopic treatment tool (including a catheter used for an insertion into the bile duct) according to the present embodiment is inserted into a treatment tool channel of an endoscope. FIG. 2 is a sideview showing a partial cross section of the endoscopic treatment tool. FIG. 3 is a view showing a cross section taken along A1-A1 line in FIG. 2. FIG. 4 is a sideview showing a partial cross section of a pre-curved shape portion of the endoscopic treatment tool when the pre-curved shape portion is in a curved state. FIG. 5 is a view showing a cross section taken along A2-A2 line in FIG. 4.

As shown in FIG. 1 and FIG. 2, an endoscopic treatment tool 1 according to the present embodiment has a shaft 2.

As shown in FIG. 2, the shaft 2 has a distal end 2a and a proximal end 2b, and the shaft 2 extends along a longitudinal axis L.

As shown in FIG. 2 and FIG. 3, the shaft 2 has a lumen tube 3 and a braid 8.

The lumen tube 3 is a tube that has at least one lumen. This lumen is used for various usages such as for inserting a guide wire, for supplying liquid such as a contrast media, and the like. For example, as shown in FIG. 3, the lumen tube 3 may be a multi-lumen tube 3x. The multi-lumen tube 3x is configured to have three lumens (a first lumen 4, a second lumen 5, and a third lumen 6).

In a case when the multi-lumen tube 3x is adopted as the lumen tube 3, the usage of each lumen is determined as follows.

The first lumen 4 is a lumen for inserting a medical guide wire (not shown).

The second lumen 5 is a lumen for transmitting the liquid such as the contrast media from the proximal end 2b to the distal end 2a of the shaft 2.

The third lumen 6 may be used as a lumen for inserting a treatment portion as well as for inserting the guide wire and transmitting the liquid such as the contrast media.

As shown in FIG. 2 and FIG. 3, the braid 8 is a tubular member surrounding the lumen tube 3. The braid 8 is disposed in the vicinity of a distal end 3a of the lumen tube 3. A distal end 8a of the braid 8 according to the present embodiment is positioned apart away from the distal end 3a by a predetermined distance at a proximal end 3b side of the lumen tube 3.

The braid 8 is formed in a tubular shape by braiding a bundle of thin wires that are formed from stainless steel in a lattice shape, for example. However, the braid 8 is not limited thereto. The braid 8 can be formed in a tubular shape by winding a stainless wire or a stainless strip in a single coil shape or a multi-threaded coil shape, and the braid 8 can be formed in a tubular shape by winding a single coil or a multi-threaded coil alternatively in different winding directions to form a multi-layer structure. In the braid 8, the shaft 2 is strengthened such that a rotation of the shaft 2 at the distal end 8a of the braid 8 can suitably follow a rotation of the shaft 2 at the proximal end 8b of the braid 8. The braid 8 is configured to realize both objects in a predetermined region in the vicinity of the distal end of the shaft 2 such that the shaft 2 has flexibility and the rotation of the distal end 2a of the shaft 2 suitably follows a rotating operation of the operator with respect to the shaft 2. According to the present embodiment, the predetermined region in the vicinity of the distal end of the shaft 2 refers to a region that is assumed to be inserted into the bile duct or the pancreatic duct during procedures using the endoscopic treatment tool 1 according to the present embodiment.

In the present embodiment, as shown in FIG. 2 and FIG. 3, a longitudinal axis L2 of the braid 8 is coaxial with the longitudinal axis L1 of the shaft 2. A length of the braid 8 in a direction along the longitudinal axis L2 of the braid 8 is determined by considering that a part at the proximal end 8b side of the braid 8 is always positioned between the duodenal papilla and the inside of the duodenum, during the procedure of inserting the shaft 2 from the distal end 2a of the shaft 2 into the bile duct and the pancreatic duct. For example, the proximal end 8b of the braid 8 is positioned at a position equal to or more than 15 centimeters spaced away from the distal end 2a of the shaft 2 at the proximal end 2b side. That is, during the procedure of inserting the shaft 2 from the distal end 2a of the shaft 2 into the bile duct and the pancreatic duct via the duodenal papilla, the region of the shaft 2 inserted into the inside of the bile duct and the pancreatic duct has a high followability with respect to the rotating operation.

Figure 16:
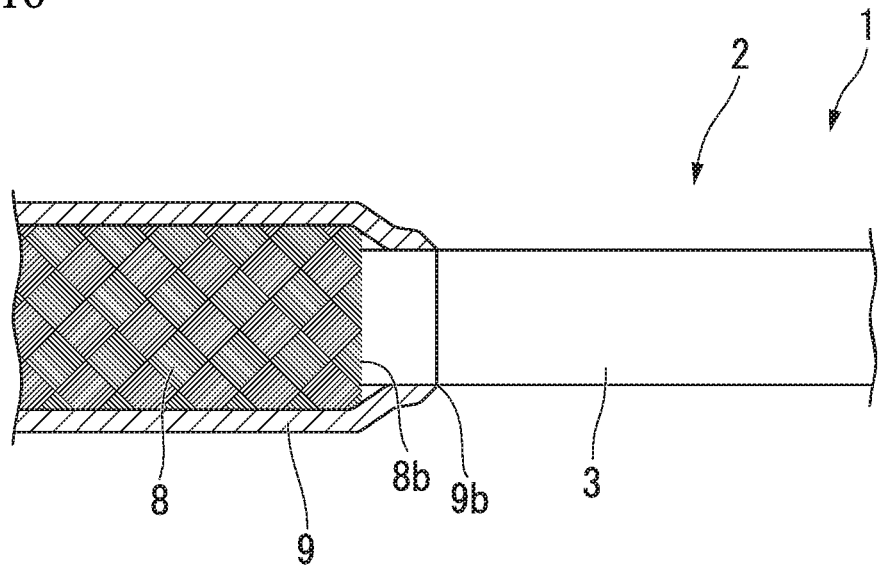
FIG. 16 is a side view showing another configuration example of the endoscopic treatment tool.

As shown in FIG. 3, FIG. 4 and FIG. 16, a coating member 9 may be configured to coat an outer circumferential surface of the braid 8. An outer circumferential surface 9c of the coating member 9 is configured to form the outer circumferential surface 2c of the shaft 2 between the distal end 9a and the proximal end 9b of the coating member 9. In this case, the coating member 9 is configured to at least coat the braid 8 between the distal end 8a of the braid 8 to the proximal end 8b of the braid 8. The coating member 9 is transparent or semi-transparent such that it is possible to capture an image of the outer circumferential surface of the braid 8 by an imaging portion (observation optical system) 102 of the endoscope 100.

On the outer circumferential surface of the braid 8, a distal indicator 11 and a proximal indictor 12 are disposed to be capable of being captured by the imaging portion 102 of the endoscope 100. Even in the case when the coating member 9 is provided on the outer circumferential surface of the braid 8, as shown in FIG. 16, the distal indicator 11 and the proximal indicator 12 can be captured by the imaging portion 102 since the coating member 9 is transparent or semitransparent.

It is not necessary for the distal indicator 11 and the proximal indicator 12 to be disposed on the outer circumferential surface of the braid 8. For example, the distal indicator 11 and the proximal indicator 12 can be disposed on the outer circumferential surface 9c of the coating member 9.

In the present embodiment, the distal indicator 11 and the proximal indicator 12 disposed on the outer circumferential surface of the braid 8, and the distal indicator 11 and the proximal indicator 12 disposed on the outer circumferential surface 9c of the coating member 9 configured to coat the outer circumferential surface of the braid 8 are described as configurations disposed on the outer circumferential surface of the braid 8.

Figure 8:
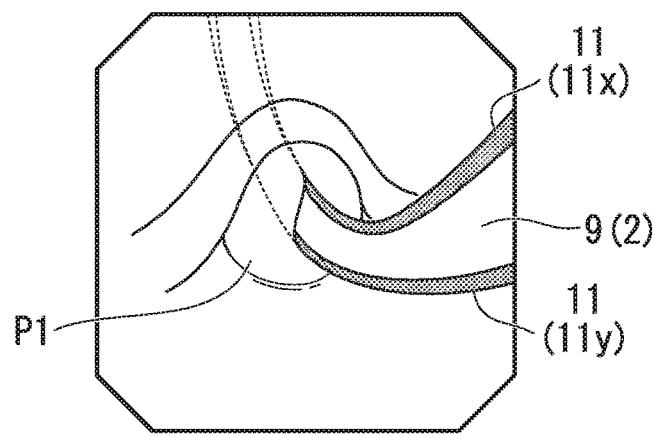
FIG. 8 is a schematic view showing the endoscopic treatment tool in the image by the endoscope in a state when a distal end of a shaft of the endoscopic treatment tool reaches a branching region of common bile duct and cystic duct.
Figure 9:
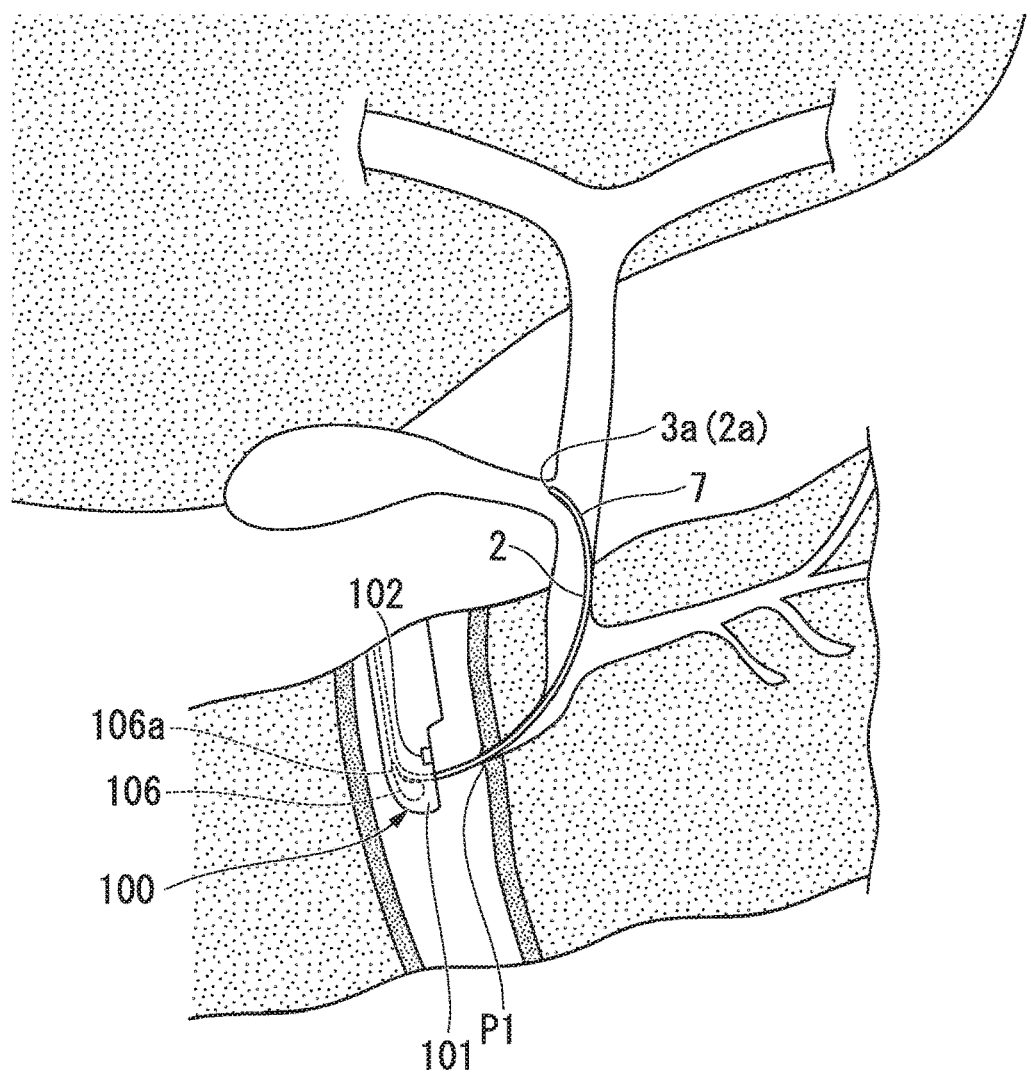
FIG. 9 is a schematic view showing the endoscopic treatment tool in the state when the distal end of the shaft of the endoscopic treatment tool reaches the branching region of the common bile duct and the cystic duct.

The distal indicator 11 is configured in considering that when the shaft 2 is rotated in the state in which the distal end 2a of the shaft 2 is inserted into the bile duct and the pancreatic duct via the duodenal papilla, the distal indicator 11 is protrudes from the duodenal papilla to be exposed in the duodenum. Specifically, in the state in which the shaft 2 is raised by a raising stand 106 of the endoscope 100 and when the distal end 2a of the shaft 2 is positioned in a branching region of the common bile duct and the cystic duct inside the body as shown in FIG. 9, the distal indicator 11 is configured to be positioned in a field of view of the imaging portion (observation optical system) 102, as shown in FIG. 8. In this case, the distal indicator 11 is disposed at least between a position of 5 centimeters from the distal end of the shaft 2 and a position of 10 centimeters from the distal end of the shaft 2. Also, the distal indicator 11 disposed between the position of 5 centimeters from the distal end of the shaft 2 and the position of 10 centimeters from the distal end of the shaft 2 may be disposed across the entire region or disposed in a local (partial) region.

The distal indicator 11 is preferable to extend along the direction of the longitudinal axis L1 of the shaft 2. That is, at least part of the distal indicator 11 is preferable to extend in a direction intersecting with the winding direction of the wires forming the braid 8.

In a case in which the distal indicator 11 is formed using a colored marker due to paint or the like, it is preferable to make the distal indicator 11 have a different color scheme from that of the outer circumferential surface of the braid 8. For example, when the color of the outer circumferential surface of the braid 8 is grey, the distal indicator 11 is preferable to be green or blue.

Figure 12:
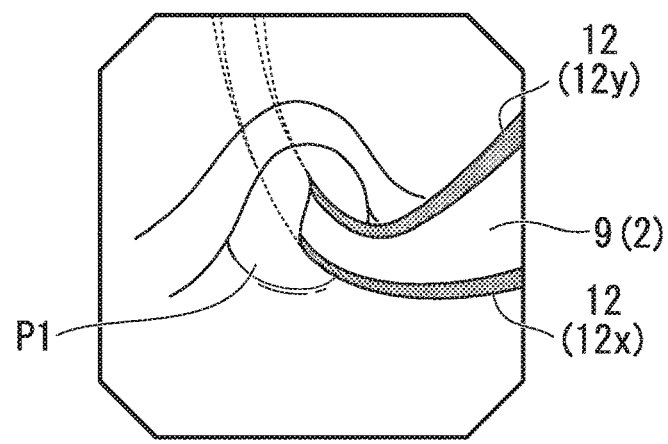
FIG. 12 is a schematic view showing the endoscopic treatment tool in the image by the endoscope in a state when the distal end of the sheath of the endoscopic treatment tool reaches a branching region of intrahepatic bile ducts.
Figure 13:
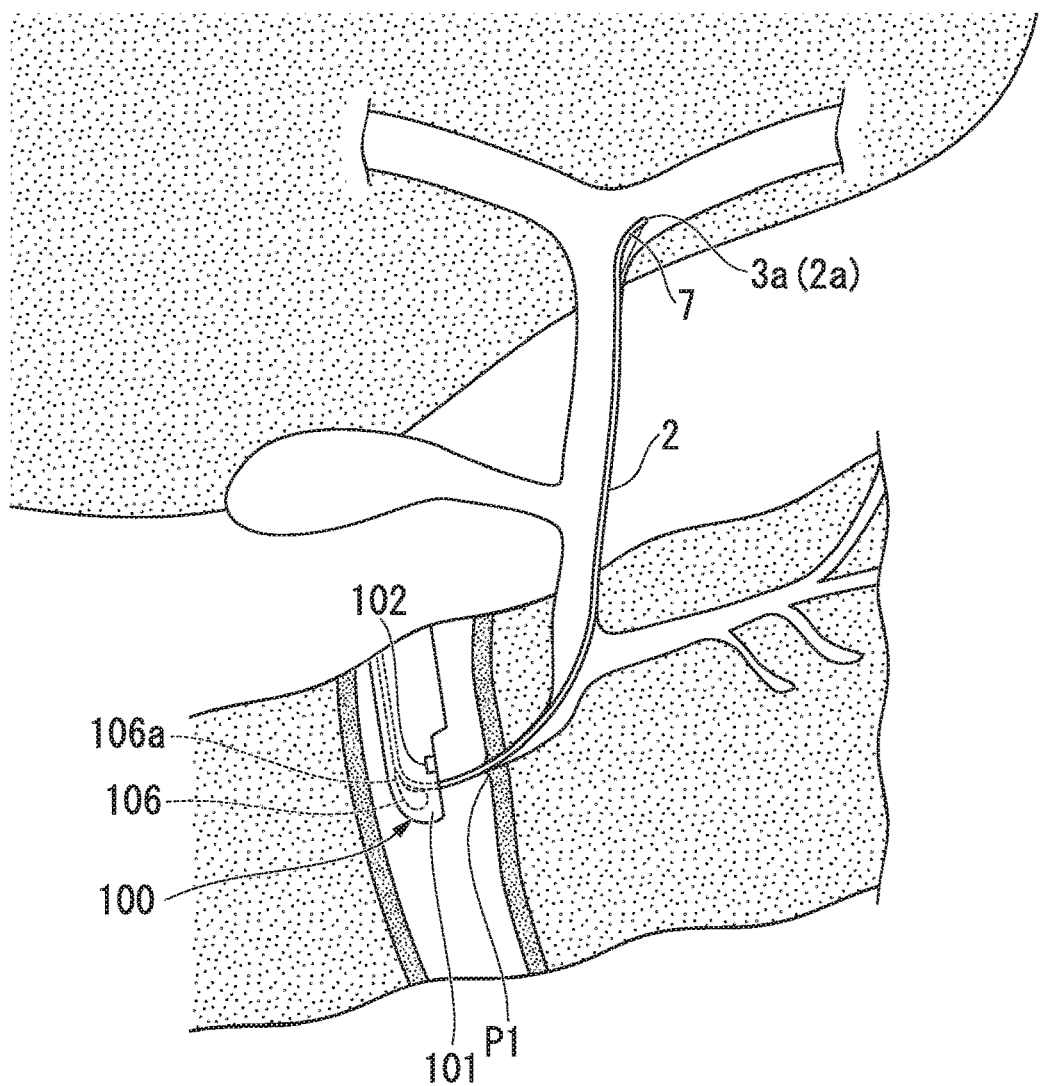
FIG. 13 is a schematic view showing the endoscopic treatment tool in the state when the distal end of the sheath of the endoscopic treatment tool reaches the branching region of the intrahepatic bile ducts.

The proximal indicator 12 is also configured in considering that when the shaft 2 is rotated in the state in which the distal end 2a of the shaft 2 is inserted into the bile duct and the pancreatic duct via the duodenal papilla, the proximal indicator 12 protrudes from the duodenal papilla to be exposed in the duodenum. Specifically, in the state in which the shaft 2 is raised by the raising stand 106 of the endoscope 100, and when the distal end 2a of the shaft 2 is positioned in a branching region of the left hepatic duct and right hepatic duct as shown in FIG. 13, the proximal indicator 12 is configured to be positioned in the field of view of the imaging portion (observation optical system) 102 as shown in FIG. 12. In this case, the proximal indicator 12 is disposed at least between a position of 10 centimeters from the distal end of the shaft 2 and a position of 15 centimeters from the distal end of the shaft 2. Also, the proximal indicator 12 disposed between the position of 10 centimeters from the distal end of the shaft 2 and the position of 15 centimeters from the distal end of the shaft 2 may be disposed across the entire region or disposed in a local (partial) region.

In a case when the shaft 2 is inserted into the duodenal papilla in a state in which the duodenal papilla is captured in the field of view of the imaging portion 102 of the endoscope 100, it is necessary to largely bend the shaft 2 in a small curvature radius by the raising stand 106 of the endoscope 100. At this time, the shaft 2 bent by the raising stand 106 is largely bent in a smaller curvature radius than that of a channel 51 which is bent due to the bending of the insert ion body 101 of the endoscope 100.

In the present embodiment, the proximal indicator 12 is configured such that in the state in which the proximal indicator 12 is positioned in the field of view of the imaging portion 102, the proximal end 8b of the braid 8 is positioned at a more proximal side of the shaft 2 than a proximal end 106a of the raising stand 106. That is, it is configured that the braid 8 which has superior flexibility and torque transmissibility is positioned in the region bent by the raising stand 106.

Accordingly, the torque transmissibility from the proximal end side to the distal end side of the shaft 2 can be maintained while maintaining the state in which the proximal indicator 12 is captured in the field of view of the imaging portion of the endoscope 100.

The proximal indicator 12 is preferable to extend along the direction of the longitudinal axis L1 of the shaft 2. That is, at least part of the proximal indicator 12 is preferable to extend in a direction intersecting with the winding direction of the wires forming the braid 8.

In a case in which the proximal indicator 12 is formed using a colored marker due to paint or the like, it is preferable to make the proximal indicator 12 have a different color scheme from that of the outer circumferential surface of the braid 8. For example, when the color of the outer circumferential surface of the braid 8 is grey, the proximal indicator 12 is preferable to be green or blue.

The distal indicator 11 and the proximal indicator 12 are preferable to be disposed in a substantial straight line.

The distal indicator 11 is more preferable configured to have a first distal indicator 11x and a second distal indicator 11y.

The proximal indicator 12 may be configured to have a first proximal indicator 12x and a second proximal indicator 12y.

As shown in FIG. 2 and FIG. 4, the first distal indicator 11x and the first proximal indicator 12x are configured to extend along the longitudinal axis L1 of the shaft 2. The first distal indicator 11x and the first proximal indicator 12x are disposed in a region equal to or less than half of the outer circumferential surface of the shaft 2 in the circumferential direction of the shaft 2. Either of a width of the first distal indicator 11x or a width of the first proximal indicator 12x is preferable to be a constant value when measured in the circumferential direction of the shaft 2 along the outer circumferential surface 2c of the shaft 2.

The second distal indicator 11y and the second proximal indicator 12y, as the same with the first distal indicator 11x and the first proximal indicator 12x, are configured to extend along the longitudinal axis L1 of the shaft 2. The second distal indicator 11y and the second proximal indicator 12y are disposed in a region equal to or less than half of the outer circumferential surface of the shaft 2 in the circumferential direction of the shaft 2. Either of a width of the second distal indicator 11y or the second proximal indicator 12y is preferable to be a constant value when measured in the circumferential direction of the shaft 2 along the outer circumferential surface of the shaft 2.

As shown in FIG. 3, the second distal indicator 11y is disposed at an opposite side with respect to the first distal indicator 11x in a radius direction of the shaft 2. As the same, the second proximal indicator 12y is disposed in an opposite side with respect to the first proximal indicator 11y in the radius direction of the shaft 2. Specifically, the second distal indicator 11y is disposed at the opposite side with respect to the first distal indicator 11x so as to sandwich the longitudinal axis (center line) L1 of the shaft 2. The second proximal indicator 12y is disposed at the opposite side with respect to the first proximal indicator 12x so as to sandwich the longitudinal axis (center line) L1 of the shaft 2.

For example, a proximal end 12b of the proximal indicator 12 may be at a position spaced away from the proximal end 2b of the shaft 2 at the distal end 2a side. For example, a distal end 11a of the distal indicator 11 may be at a position spaced away from the distal end 2a of the shaft 2 at the proximal end 2b side.

The distal indicator 11 may be in the vicinity of the distal end 8a of the braid 8, for example, the distal indicator 11 may be at a position slightly spaced away from the distal end 8a of the braid 8 at the proximal end 2b side of the shaft 2.

As shown in FIG. 4, for example, the width of the distal indicator 11 measured in the circumferential direction of the shaft 2 along the outer circumferential surface of the shaft 2, may be equal to the width of the proximal indicator 12 measured in the circumferential direction of the shaft 2 along the outer circumferential surface of the shaft 2.

In the present embodiment, the first distal indicator 11x and the second distal indicator 11y are not continuous in the circumferential direction of the shaft 2. That is, in the circumferential direction of the shaft 2, there is a gap generated between the first distal indicator 11x and the second distal indicator 11y. Also, the first proximal indicator 12x and the second proximal indicator 12y are not continuous in the circumferential direction of the shaft 2. That is, there is a gap generated between the first proximal indicator 12x and the second proximal indicator 12y.

The first distal indicator 11x and the second distal indicator 11y are not limited thereto. The first distal indicator 11x and the second distal indicator 11y may be disposed in the circumferential direction of the shaft 2 so as to be adjacent to each other without any gap. In this case, when the paint colored marker is used, the color of the first distal indicator 11x is different from the color of the second distal indicator 11y such that a boundary of the first distal indicator 11x and the second distal indicator 11y can be recognized on the image captured by the endoscope.

The first proximal indicator 12x and the second proximal indicator 12y are the same as the first distal indicator 11x and the second distal indicator 11y which are described above. That is, the first proximal indicator 12x and the second proximal indicator 12y may be disposed in the circumferential direction of the shaft 2 so as to be adjacent to each other without any gap. When the paint colored marker is used, the color of the first proximal indicator 12x is different from the color of the second proximal indicator 12y such that a boundary of the first proximal indicator 12x and the second proximal indicator 12y can be recognized on the image captured by the endoscope.

The endoscopic treatment tool 1 according to the present embodiment may have a pre-curved shape portion 7 having a predetermined curved shape that is disposed in the vicinity of a distal end 3a of the lumen tube 3 as shown in FIG. 4. In this case, for example, the pre-curved shape portion 7 is disposed between the distal end 11a of the distal indicator 11 and the distal end 2a of the shaft 2.

The pre-curved shape portion 7 is configured to have a predetermined curving habit with respect to the lumen tube 3. That is, the pre-curved shape portion 7 has a restoring force so as to restore to the predetermined curved shape. Accordingly, after the pre-curved shape portion 7 is deformed to a straight shape when being applied with an external force, once the external force is withdrawn, the pre-curved shape portion 7 can restore to the original curved shape.

Furthermore, the curved shape of the pre-curved shape portion 7 is configured in consideration of changing the orientation of the shaft 2 such that the distal end 2a of the shaft 2 can be easily inserted into the duodenal papilla, in a case when the shaft 2 is protruded from the distal end of a treatment tool channel 103 of a sideview type endoscope 100 (see FIG. 1).

When the pre-curved shape portion 7 is disposed in the vicinity of the distal end 3a of the lumen tube 3, as shown in FIG. 4, the distal end 8a of the braid 8 is positioned at a side closer to the proximal end 3b than the proximal end 7b of the pre-curved shape portion 7.

As shown in FIG. 4 and FIG. 5, the first distal indicator 11x and the first proximal indicator 12x are associated with the shape of the pre-curved shape portion 7 of the shaft 2. The distal end 2a of the shaft 2 is positioned in the range defined by the width of the first distal indicator 11x and the first proximal indicator 12x, in a front view along the direction of the longitudinal axis L1 of the shaft 2. That is, in the front view along the direction of the longitudinal axis L1 of the shaft 2a, a direction X1 orthogonal to the longitudinal axis L1 of the shaft 2 and from the longitudinal axis L1 toward the first distal indicator 11x and the first proximal indicator 12x is substantially coincides with the bending direction of the pre-curved shape portion 7.

Further, as shown in FIG. 4 and FIG. 5, the second distal indicator 11y and the second proximal indicator 12y are associated with the shape of the pre-curved shape portion 7 of the shaft 2. The distal end 2a of the shaft 2 is positioned in the range defined by the width of the second distal indicator 11y and the second proximal indicator 12y, in a front view along the direction of the longitudinal axis L1 of the shaft 2. That is, in the front view along the direction of the longitudinal axis L1 of the shaft 2a, a direction X2 orthogonal to the longitudinal axis L1 of the shaft 2 and from the longitudinal axis L1 toward the second distal indicator 11y and the second proximal indicator 12y is opposite to the bending direction of the pre-curved shape portion 7.

As shown in FIG. 2, the endoscopic treatment tool according to the present embodiment may have a treatment portion 13 and an operation portion 20. The treatment portion 13 is provided at the distal side of the shaft 2, and the operation portion 20 is provided at the proximal side of the shaft 2. The treatment portion 13 has a knife fixing portion 18 fixed to the vicinity of the distal end 3a of the multi-lumen tube 3x (knife support portion 14) and a knife wire 15 connected to the knife fixing portion 18.

In this case, the third lumen 6 may be used as the lumen into which the knife wire 15 of the treatment portion 13 is inserted.

As shown in FIG. 2 and FIG. 3, two through holes 6a, 6b are formed in the vicinity of the distal end of the third lumen 6 so as to be spaced away from each other in the direction of the longitudinal axis L1 of the shaft 2. Either of the two through holes 6a, 6b is communicated with the third lumen 6 and opens on the outer circumferential surface of the multi-lumen tube 3x. The knife wire 15 is inserted into the two through holes 6a, 6b. In the two through holes 6a, 6b, the through hole 6a formed at the distal end 2a side of the shaft 2 is at a position slightly away from the distal end 2a of the shaft 2 at the proximal end 2b side. In the two through holes 6a, 6b, the through hole 6b formed at the proximal end 2b side of the shaft 2 is at a position at a side closer to the distal end 2a of the shaft 2 than the distal end 8a of the braid 8. A distance between the two through holes 6a, 6b in the direction along the longitudinal axis L1 of the shaft 2 may be about 30 millimeters, for example.

The openings of the two through holes 6a, 6b are toward the inward side (inward circumferential side) of the curved shape of the pre-curved shape portion 7.

For example, in the direction along the longitudinal axis L1 of the shaft 2, the distal end 11a of the distal indicator 11 is positioned in the vicinity of the proximal side through hole 6b formed on the multi-lumen tube 3, and the distal end 11a of the distal indicator 11 is more proximal than the through hole 6b.

The knife wire 15 has a knife portion 16 and a conductive wire portion 17, wherein the knife portion 16 is connected to the knife fixing portion 18 and disposed outside the multi-lumen tube 3x, and the conductive wire portion 17 is configured to extend to the proximal end 2b of the shaft 2 via the third lumen 6 of the multi-lumen tube 3x. The knife wire 15 is connected to the multi-lumen tube 3x by the knife fixing portion 18 at the distal side through hole 6a of the two through holes 6a, 6b which are disposed in the vicinity of the distal end 3a of the multi-lumen tube 3x. That is, a distal end of the knife wire 15 is fixed to the vicinity of the distal end of the shaft 2 (knife support portion 14) by the knife fixing portion 18. The knife portion 16 is exposed to the outside of the multi-lumen tube 3x in the region between the two through holes 6a, 6b which are disposed in the vicinity of the distal end 3a of the multi-lumen tube 3x.

In the present embodiment, the knife portion 16 and the conductive knife portion 17 are configured by the knife wire 15 which is formed by a continuous metal wire. Accordingly, there is not a clear boundary between the knife portion 16 and the conductive knife portion 17. In the present embodiment, the knife portion 16 refers to the part exposed to the outside of the multi-lumen tube 3x between the two through holes 6a, 6b which are formed in the vicinity of the distal end 3a of the multi-lumen tube 3x.

Between the two through holes formed on the multi-lumen tube 3x, the knife wire 15 is disposed at a position spaced away from a center (the position of the longitudinal axis L1) of the shaft 2 in a section orthogonal to the longitudinal axis L1 of the shaft 2. The distal end portion of the shaft 2 including the distal side through hole 6a is actively bendable by pulling the knife wire 15 at the operation portion side.

In the front view from the direction along the longitudinal axis L1 of the shaft 2, the distal end portion bent by pulling the knife wire 15 at the operation portion side is substantially coincided with the position where the knife portion 16 is exposed from the shaft 2. Also, in a projection plane formed on a plane orthogonal to the longitudinal axis L1 of the shaft 2, the distal indicator 11 and the proximal indicator 12 substantially coincides with the position where the knife portion 16 is exposed from the shaft 2.

As shown in FIG. 1 and FIG. 2, the operation portion 20 has a main body 21 and a slider 26.

The main body 21 has a guide wire port 22, a liquid port 23, and an axial portion 24.

The guide wire port 22 communicates with the first lumen 4 of the shaft 2.

The liquid port 23 communicates with the second lumen 5 of the shaft 2.

The axial portion 24 is formed in a rod shape and the axial portion 24 has a finger hook ring 25 at an end.

The slider 26 is connected to the axial portion 24 so as to be capable of advancing and retracting with respect to the axial portion 24. The slider 26 has a finger hook ring 27 and a plug 28.

The plug 28 provided at the slider 26 is connected to the proximal end 15b of the knife wire 15 (the proximal end 17b of the conductive wire portion 17). Accordingly, it is possible to flow a high-frequency current to the conductive wire portion 17 through the knife portion 16 by connecting the plug 28 with a high-frequency power supply (not shown).

The endoscope 100 used with the endoscopic treatment tool 1 according to the present embodiment will be described.

The endoscope 100 used with the endoscopic treatment tool 1 is a flexible side-view type endoscope, as shown in FIG. 1. For example, the endoscope 100 has an elongated insertion body 101, and an operation body 104 disposed at an end portion of the insertion body 101.

A side-view type imaging portion 102 is disposed at a distal end 101a of the insertion body 101 such that a center of a field of view is directed to a direction intersecting a center line of the insertion body 101. Also, a distal opening 103a of a treatment tool channel 103 for inserting the shaft 2 of the endoscopic treatment tool 1 is formed at the distal end 101a of the insertion body 101.

The operation body 104 has a knob 105 for controlling the bending operation of the insertion body 101 and a proximal opening 103b of the treatment tool channel 103.

The effect of the endoscopic treatment tool 1 according to the present embodiment will be described.

Figure 6:
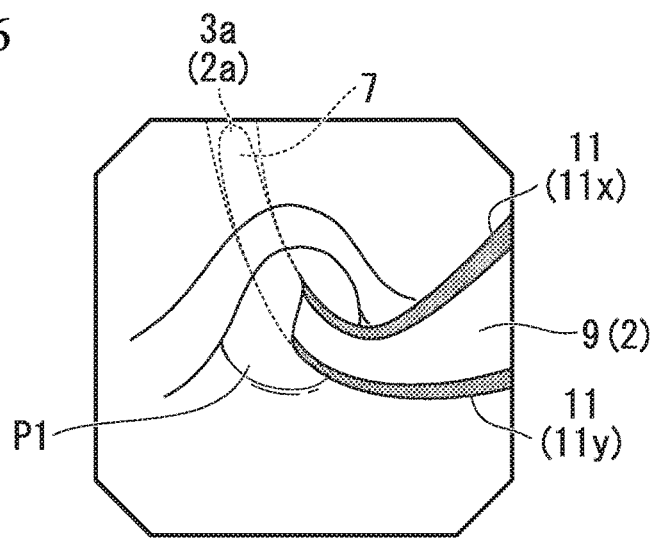
FIG. 6 is a schematic view showing the endoscopic treatment tool in an image by the endoscope in a state when the endoscopic treatment tool is inserted into the bile duct via the duodenal papilla.
Figure 7:
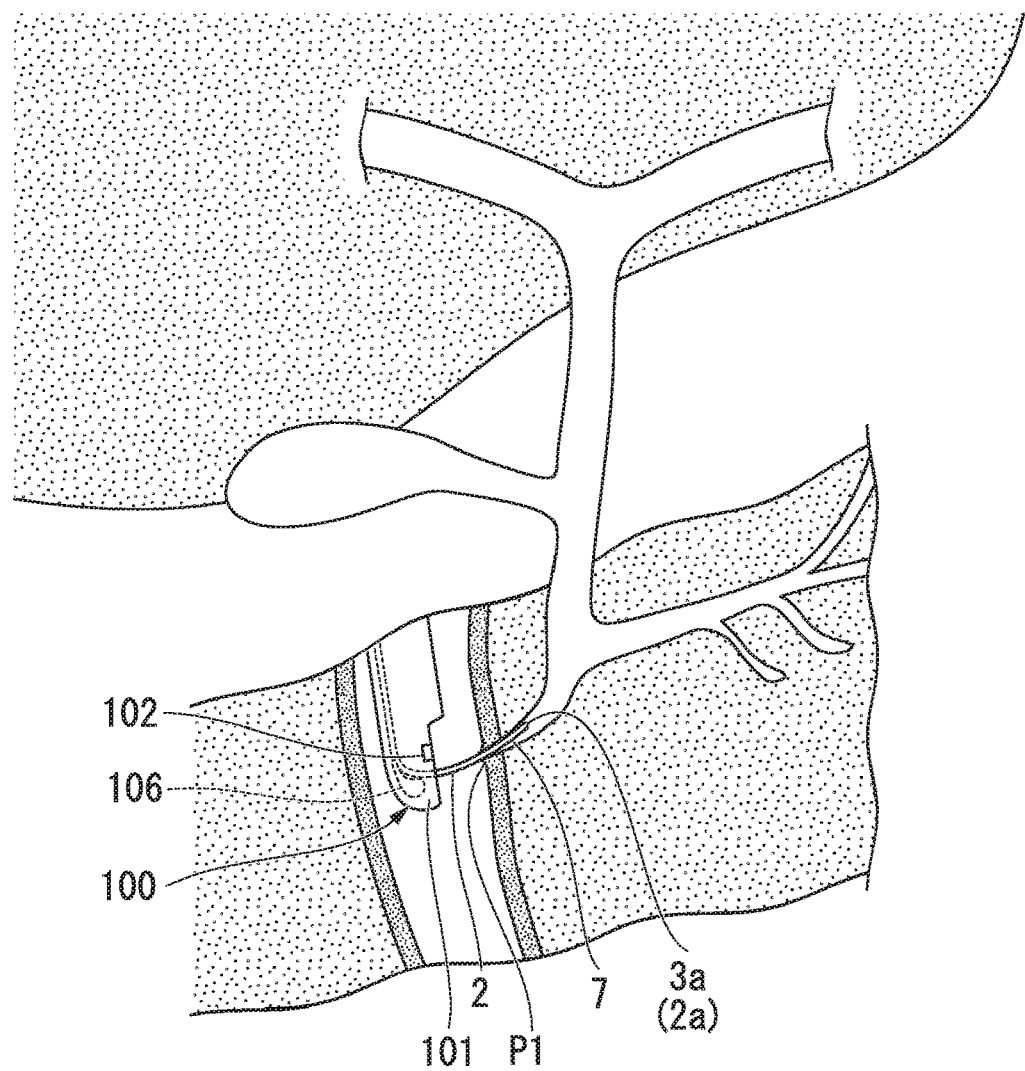
FIG. 7 is a schematic view showing the endoscopic treatment tool in the state when the endoscopic treatment tool is inserted into the bile duct via the duodenal papilla.

FIG. 6 is a schematic view showing the endoscopic treatment tool in an image captured by the endoscope in a state when the endoscopic treatment tool is inserted into the bile duct via the duodenal papilla. FIG. 7 is a schematic view showing the endoscopic treatment tool in the state when the endoscopic treatment tool is inserted into the bile duct via the duodenal papilla.

In the present embodiment, the operator (for example, a scopist) inserts the endoscope 100 into the mouth, and then guides the distal end 101a of the insertion body 101 of the endoscope 100 to the vicinity of the duodenal papilla (shown as the reference sign P in the figure) (see FIG. 7).

During the procedure of using the endoscopic treatment tool 1, the operator (for example, the surgeon) inserts the shaft 2 of the endoscopic treatment tool 1 into the treatment tool channel 103 of the endoscope 100, protrudes the distal end 2a of the shaft 2 from the distal opening 103a of the treatment tool channel 103, and inserts the distal end 2a of the shaft 2 into the duodenal papilla.

As shown in FIG. 6, the position and the orientation of the distal end 2a of the endoscopic treatment tool 1 is observable using the imaging portion 102 of the endoscope 100 until the shaft 2 enters the duodenal papilla. However, after the shaft 2 enters the duodenal papilla, the part of the shaft 2 that has entered the duodenal papilla cannot be observed using the imaging portion 102 of the endoscope 100.

The operator can observe the shaft 2 that enters the bile duct and the pancreatic duct using an X-ray image. For example, as shown in FIG. 7, the operator can observe a movement of the shaft 2 using the X-ray image. On the X-ray image, the member having radiopacity (for example, the knife wire 15 made from metal) can be clearly visually confirmed. Also, it is possible to understand the position and the orientation of the shaft 2 using the X-ray image if the shaft 2 is made from the material having radiopacity.

However, in the case of rotating the shaft 2 about the longitudinal axis L1 of the shaft 2 as the rotation center, it is difficult to understand how much the distal end 2a of the shaft 2 has rotated by confirming the X-ray image. Also, in the case of rotating the shaft 2 protruding from the proximal opening 103b formed at the operation body 104 of the endoscope 100, an operating amount of rotating the shaft 2 does not coincide with a rotation movement amount of the distal end 2a of the shaft 2 due to the flexibility of the shaft 2. In the entire length of the shaft 2, the range from the proximal end 2b of the shaft 2 to the proximal end 8b of the braid 8 is elongated such that a discrepancy between the operating amount of rotating the shaft 2 and the rotation movement amount of the distal end 2a of the shaft 2 is large. In the range from the proximal end 8b of the braid 8 to the distal end 2a of the shaft 2, since the range from the proximal end 8b of the braid 8 to the distal end 2a of the shaft 2 is shorter than the range from the proximal end 2b of the shaft 2 to the proximal end 8b of the braid 8 and the rotation followability is enhanced by the braid 8, the discrepancy between the operating amount of rotating the shaft 2 and the rotation movement amount of the distal end 2a of the shaft 2 is small.

In the endoscopic treatment tool 1 according to the present embodiment, the distal indicator 11 and the proximal indicator 12 are provided such that it is easy to assume the rotation position of the distal end 2a of the shaft 2 based on the positions of the distal indicator 11 and the proximal indicator 12, even if the orientation of the distal end 2a of the shaft 2 cannot be understood using the imaging portion 102 of the endoscope 100.

Figure 10:
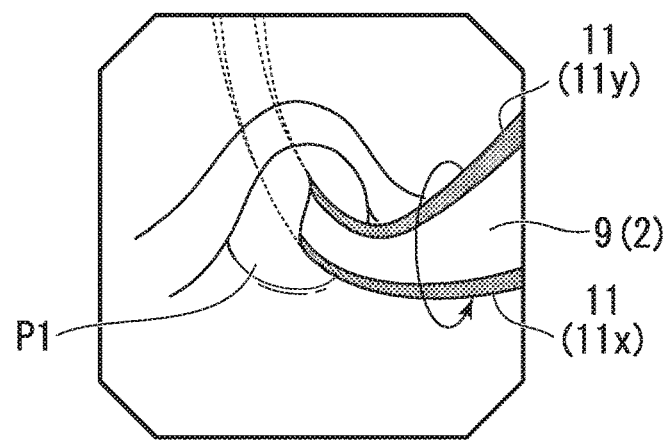
FIG. 10 is a schematic view showing the endoscopic treatment tool in the image by the endoscope in a state when a distal end of a sheath of the endoscopic treatment tool is rotated in the branching region of the common bile duct and the cystic duct.
Figure 11:
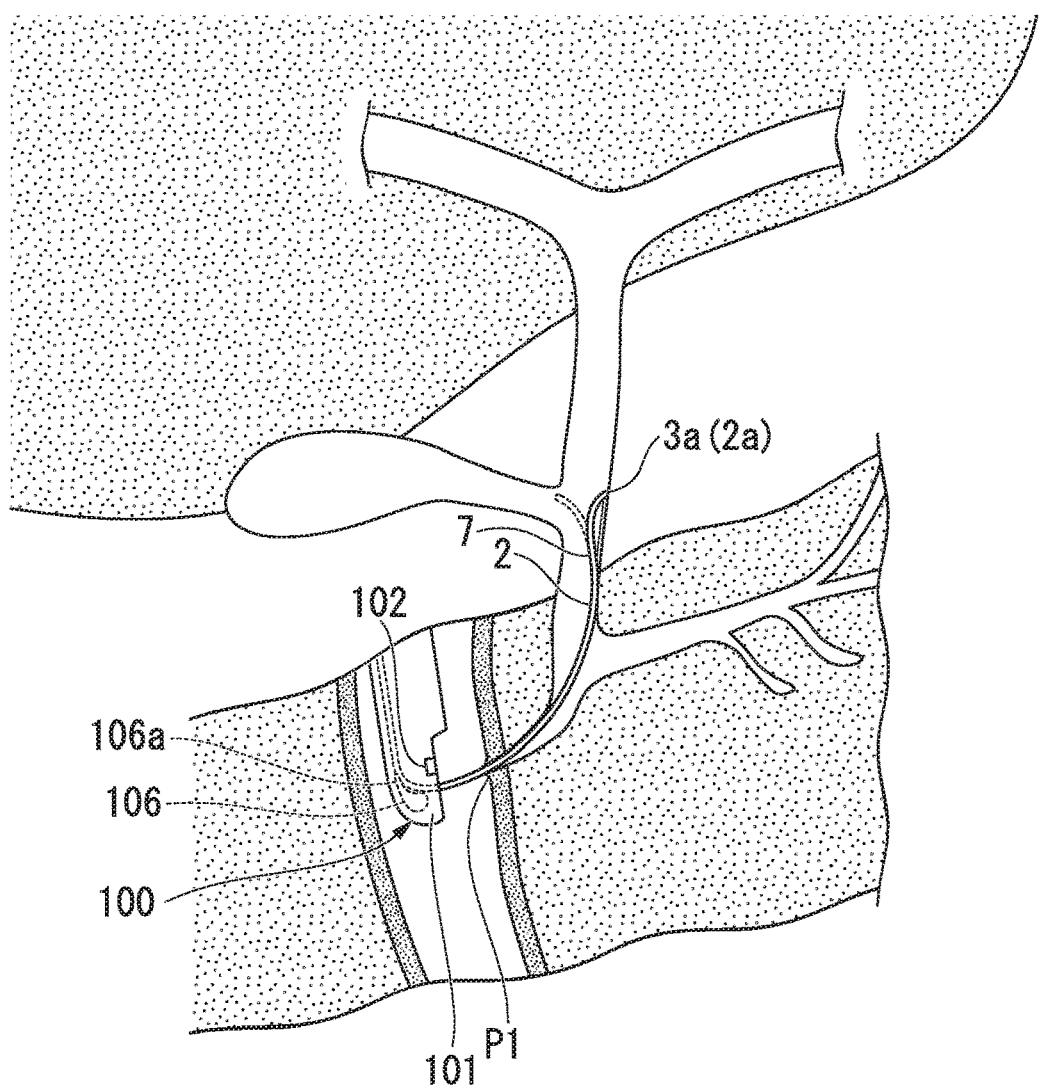
FIG. 11 is a view showing the endoscopic treatment tool in the state when the distal end of the sheath of the endoscopic treatment tool is rotated in the branching region of the common bile duct and the cystic duct.

FIG. 8 is a schematic view showing the endoscopic treatment tool in the image captured by the endoscope in a state when a distal end of a shaft of the endoscopic treatment tool reaches a branching region of common bile duct and cystic duct. FIG. 9 is a schematic view showing the endoscopic treatment tool in the state when the distal end of the shaft of the endoscopic treatment tool reaches the branching region of the common bile duct and the cystic duct. FIG. 10 is a schematic view showing the endoscopic treatment tool in the image captured by the endoscope in a state when a distal end of a sheath of the endoscopic treatment tool is rotated in the branching region of the common bile duct and the cystic duct. FIG. 11 is a view showing the endoscopic treatment tool in the state when the distal end of the sheath of the endoscopic treatment tool is rotated in the branching region of the common bile duct and the cystic duct.

As shown in FIG. 9, after the distal end 2a of the shaft 2 reaches the branching region of the common bile duct and the cystic duct, there are a case of inserting the shaft 2 into the intrahepatic bile duct through the common bile duct and a case of inserting the shaft 2 into the cystic duct. If the shaft 2 is inserted into the duct with the original state, due to a meandering state of the shaft 2 in the duct, the shaft 2 may be inserted into a different duct from the duct into which the shaft 2 is intended to be inserted among the branched ducts. In this case, it is necessary for the operator to rotate the shaft 2 for directing the orientation of the distal end 2a of the shaft 2 toward the duct into which the shaft 2 is intended to be inserted (the intrahepatic bile duct side or the cystic duct side).

As shown in FIG. 10, once the shaft 2 is rotated, as shown in FIG. 11, the direction of the distal end 2a of the shaft 2 can be changed. Accordingly, the operator can direct the distal end 2a of the shaft 2 toward the direction of the duct into which the distal end 2a of the shaft 2 is intended to be inserted.

In the endoscopic treatment tool 1 according to the present embodiment, when the distal end 2a of the shaft 2 is positioned at the branched region of the common bile duct and the cystic duct, since the distal indicator 11 is protruded from the duodenal papilla into the duodenum, the duodenal papilla and the vicinity thereof can be captured in the field of view of the imaging portion 102. Accordingly, the operator can understand the rotation state of the shaft 2 by confirming the positions of the distal indicator 11, more specifically, the first distal indicator 11x and the second distal indicator 11y, in the circumferential direction using the image captured by the endoscope.

Figure 14:
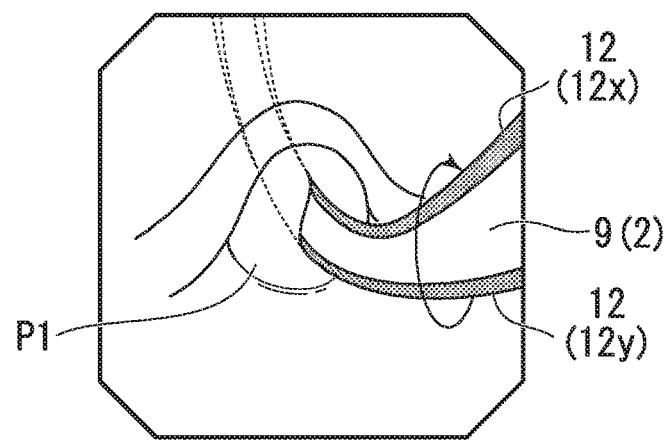
FIG. 14 is a schematic view showing the endoscopic treatment tool in the image by the endoscope in the state when the distal end of the sheath of the endoscopic treatment tool is rotated in the branching region of the intrahepatic bile ducts.
Figure 15:
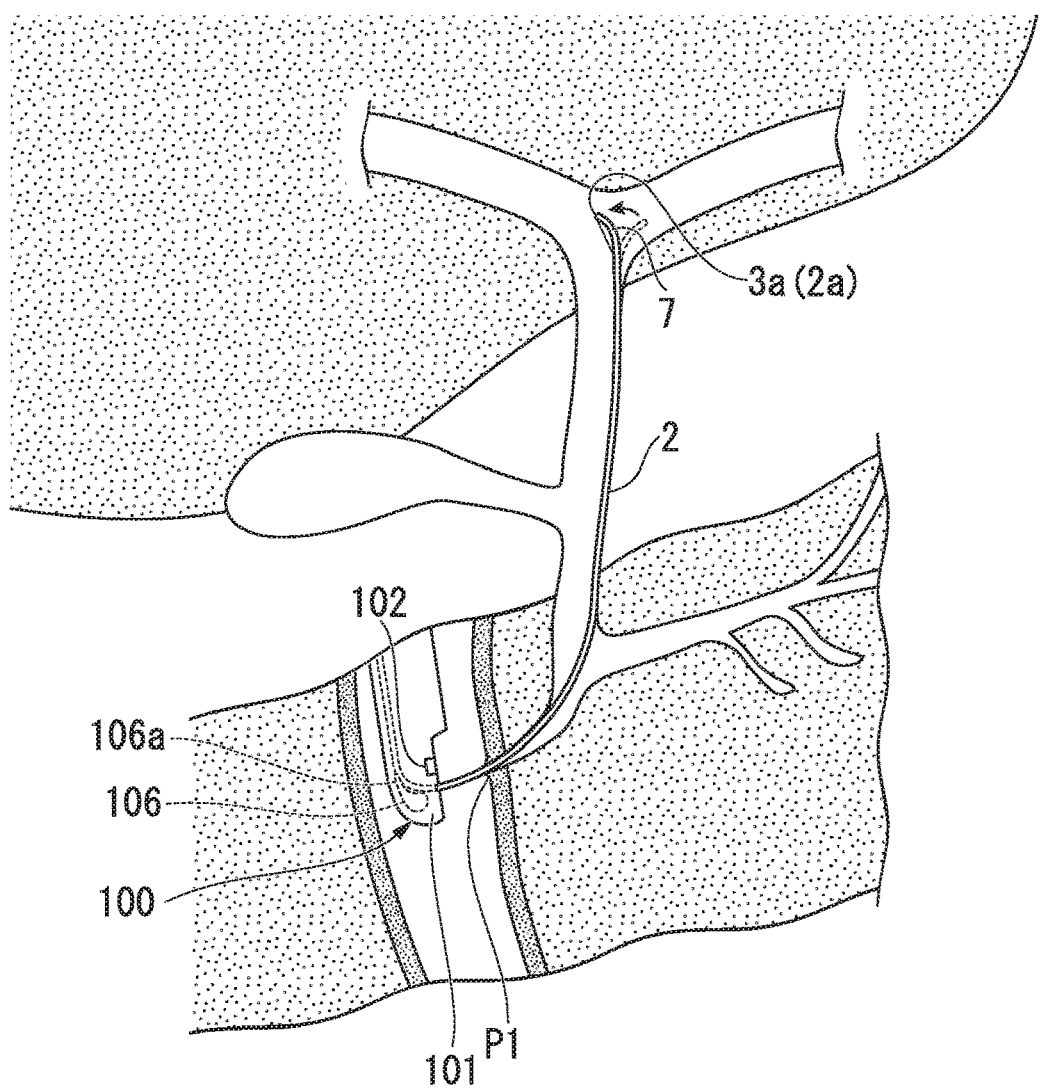
FIG. 15 is a schematic view showing the endoscopic treatment tool in the state when the distal end of the sheath of the endoscopic treatment tool is rotated in the branching region of the intrahepatic bile ducts.

FIG. 13 is a schematic view showing the endoscopic treatment tool in the state when the distal end of the sheath of the endoscopic treatment tool reaches the branching region of the intrahepatic bile ducts. FIG. 14 is a schematic view showing the endoscopic treatment tool in the image by the endoscope in the state when the distal end of the sheath of the endoscopic treatment tool is rotated in the branching region of the intrahepatic bile ducts. FIG. 15 is a schematic view showing the endoscopic treatment tool in the state when the distal end of the sheath of the endoscopic treatment tool is rotated in the branching region of the intrahepatic bile ducts.

Once the distal end 2a of the shaft 2 is moved toward the intrahepatic bile duct, the distal end 2a of the shaft 2 reaches the branching region of the intrahepatic bile ducts. As shown in FIG. 13, after the distal end 2a of the shaft 2 reaches the branching region of the left hepatic duct and the right hepatic duct, there are a case of inserting the shaft 2 into the left hepatic duct and a case of inserting the shaft 2 into the right hepatic duct. If the shaft 2 is inserted into the duct in the original state, due to the meandering state of the shaft 2 in the duct, the shaft 2 may be inserted into a different duct from the duct into which the shaft 2 is intended to be inserted among the branched ducts. In this case, it is necessary for the operator to rotate the shaft 2 for directing the orientation of the distal end 2a of the shaft 2 toward the duct into which the shaft 2 is intended to be inserted (the left hepatic duct side or the right hepatic duct side).

As shown in FIG. 14, once the shaft 2 is rotated, as shown in FIG. 15, the direction of the distal end 2a of the shaft 2 can be changed. Accordingly, the operator can direct the distal end 2a of the shaft 2 toward the direction of the duct into which the distal end 2a of the shaft 2 is intended to be inserted.

In the endoscopic treatment tool 1 according to the present embodiment, when the distal end 2a of the shaft 2 is positioned at the branched region of the left hepatic duct and the right hepatic duct, since the proximal indicator 12 is protruded from the duodenal papilla into the duodenum so as to be captured in the field of view of the imaging portion 102. Accordingly, the operator can understand the rotation state of the shaft 2 by confirming the positions of the proximal indicator 12, more specifically, the first proximal indicator 12x and the second proximal indicator 12y, in the circumferential direction using the image captured by the endoscope.

In the shaft 2 according to the present embodiment, the distal indicator 11 and the proximal indicator 12 are provided on the outer circumferential surface of the braid 8 such that the region where the first indicator 11 and the proximal indicator 12 are disposed has superior rotation followability. Accordingly, the discrepancy between the rotation amount of the distal indicator 11 and the rotation amount of the distal end 2a of the shaft 2 is small. Also, the discrepancy between the rotation amount of the proximal indicator 12 and the rotation amount of the distal end 2a of the shaft 2 is small. In other words, the rotation amounts of the distal indicator 11 and the proximal indicator 12 can be presumed as the rotation amount of the distal end 2a of the shaft 2.

As a result, the operator can assume how much the distal end 2a of the shaft 2 has rotated with higher accuracy by observing the image captured by the endoscope regarding how much the distal indicator 11 and the proximal indicator 12 have rotated in correspondence with the operation of rotating the shaft 2.

The position and the orientation of the shaft 2 can be assumed with higher accuracy by confirming the X-ray image in combination.

As shown in FIG. 4, in a case in which the pre-curved shape portion 7 is disposed in the vicinity of the distal end 3a of the lumen tube 3, the same effect can be achieved. Further, in a case in which the treatment portion 13 is disposed at the distal end side of the shaft 2 and the operation portion 20 is disposed at the proximal end side of the shaft 2, the same effect can be achieved.

Each indicator is associated with the shape of the pre-curved shape portion 7 such that the first distal indicator 11x and the first proximal indicator 12x are corresponding to the bending direction of the pre-curved shape portion 7 and the second distal indicator 11y and the second proximal indicator 12y are corresponding to the opposite direction of the bending direction of the pre-curved shape portion 7. As a result, according to the endoscopic treatment tool 1 according to the present embodiment, it is easy to understand the orientation of the endoscopic treatment tool 1 inserted into the bile duct and the pancreatic duct using the image captured by the endoscope, and thus it is possible to minimize the operation of rotating the shaft 2.

Since the bending shape of the pre-curved shape portion 7 is associated with the distal indicator 11 and the proximal indicator 12, in the state when the shaft 2 is inserted into the bile duct and the pancreatic duct through the duodenal papilla, it is easy for the operator to understand the direction of the distal end 2a of the shaft 2 by considering the positions of the distal indicator 11 and the proximal indicator 12 on the image captured by the endoscope, and the direction of the shaft 2 on the X-ray image.

As described above, according to the endoscopic treatment tool 1 of the present embodiment, it is easy to understand the orientation of the endoscopic treatment tool 1 using the image captured by the endoscope.

The embodiments of the invention have been described above with reference to the drawings, but specific structures of the invention are not limited to the embodiments and may include various modifications without departing from the scope of the invention.

Figure 17:
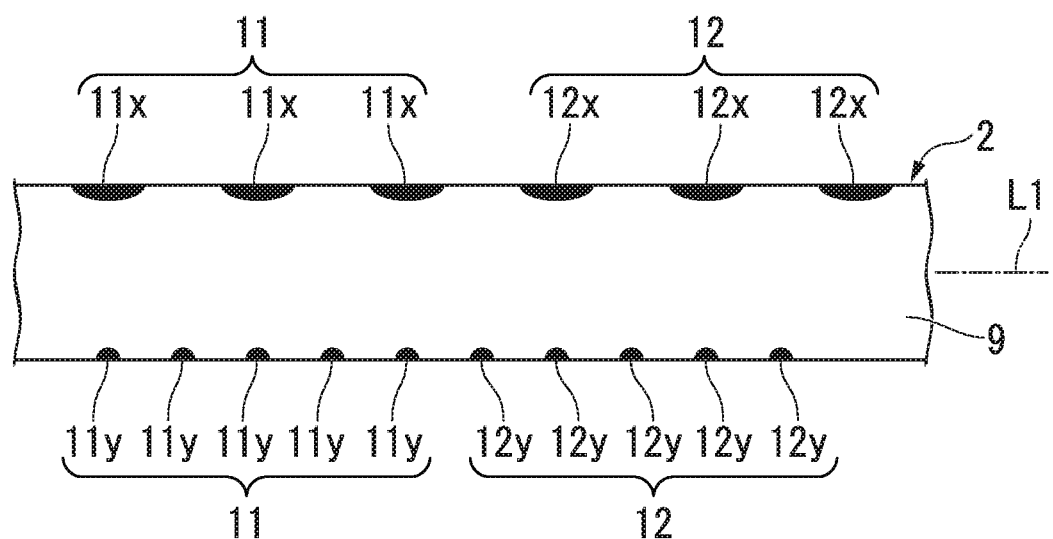
FIG. 17 is a side view showing a further configuration example of the endoscopic treatment tool.

For example, as shown in FIG. 17, the distal indicator 11 and the proximal indicator 12 according to the above embodiment may be discontinuous along the longitudinal direction of the shaft 2. For example, the distal indicator 11 and the proximal indicator 12 may be configured by arranging a plurality of dots at intervals in the direction along the longitudinal axis L1 of the shaft 2 to forma dot pattern. In this case, the dot pattern may be at even intervals, and the dot pattern may be at uneven intervals.

Figure 18:
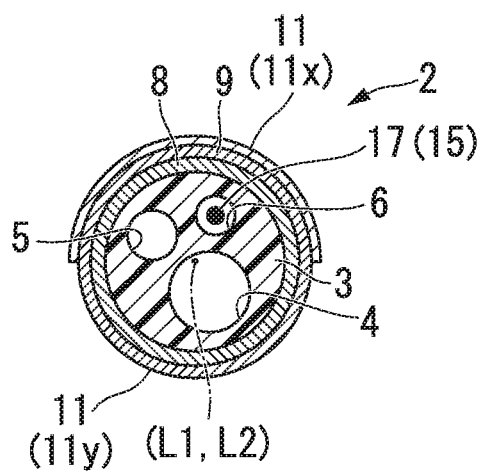
FIG. 18 is a side view showing a further configuration example of the endoscopic treatment tool.

As shown in FIG. 18, in the case when each of the first distal indicator 11x and the second distal indicator 11y has a width equal to half of the shaft 2 in the circumferential direction of the shaft 2 respectively and the first distal indicator 11x and the second distal indicator 11y are adjacent to each other, either of the first distal indicator 11x or the second distal indicator 11y (the first distal indicator 11x in FIG. 18) may be colored with a different color from that of the material of the shaft 2, and the other (the second distal indicator 11y in FIG. 18) may be formed from the material of the shaft 2 (the color of the coating member 9 in FIG. 18). That is, the part on the outer circumferential surface of the shaft 2 that is colored becomes the first distal indicator 11x, and the part that is not colored becomes the second distal indicator 11y. The first proximal indicator 12x and the second proximal indicator 12y may have the same configurations.

Figure 19:
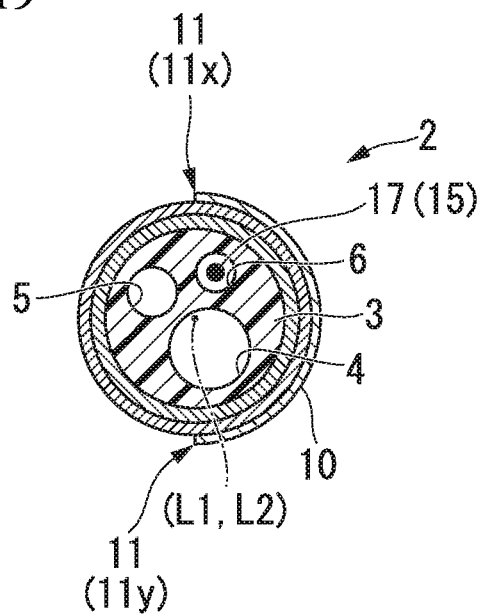
FIG. 19 is a side view showing a further configuration example of the endoscopic treatment tool.

As shown in FIG. 19, half of the shaft 2 in the circumferential direction of the shaft 2 is colored with a first color (reference sign 10 in FIG. 19), and the other half of the shaft 2 in the circumferential direction of the shaft 2 is colored with another color different from the first color (for example, the color of the coating member 9), thus the boundaries of the first color and the other color may be defined as the first distal indicator 11x and the second distal indicator 11y. The first proximal indicator 12x and the second proximal indicator 12y may have the same configurations.

The distal indicator 11 and the proximal indicator 12 may be configured by using the paint having radiopacity. In this case, the distal indicator and the proximal indicator can be confirmed on the X-ray image such that the torsion state of the sheath inside the bile duct and the pancreatic duct is easy to understand.

Second Embodiment

Figure 20:
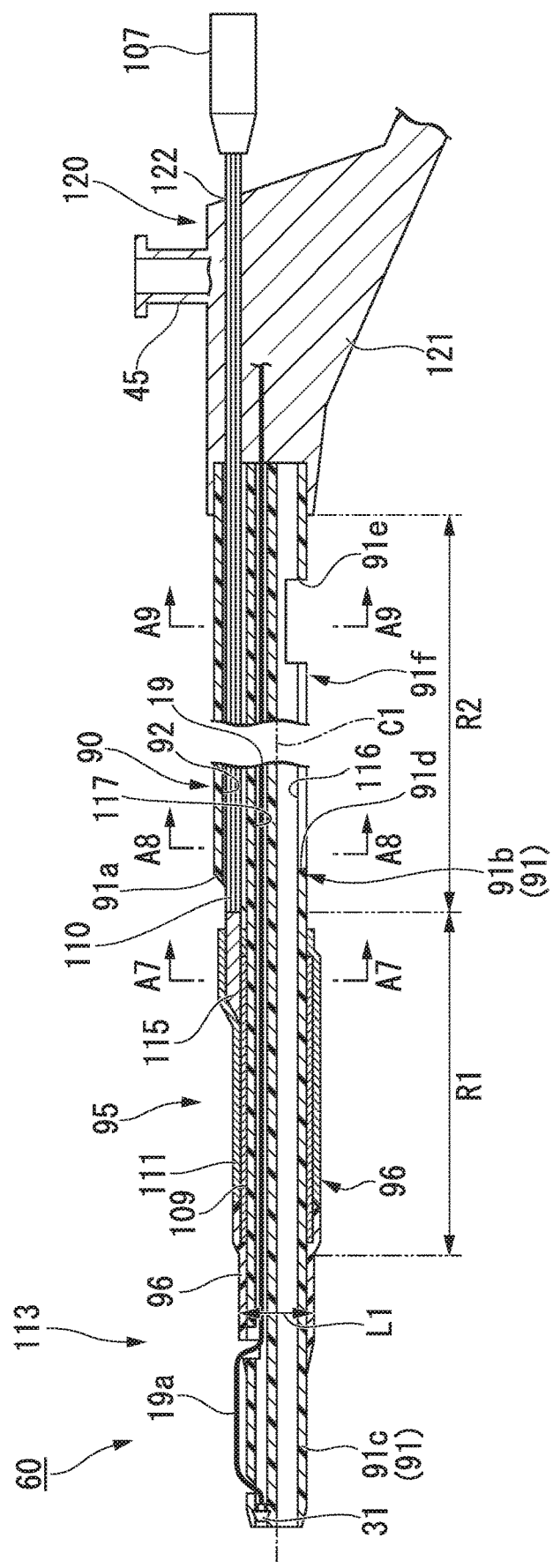
FIG. 20 is a side view showing a cross section of an endoscopic treatment tool according to a second embodiment of the present invention.
Figure 21:
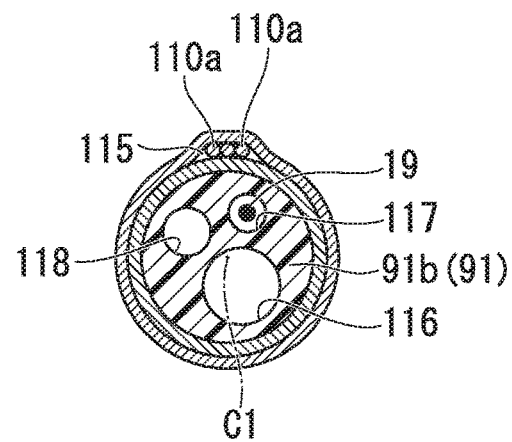
FIG. 21 is a view showing a cross section taken along A7-A7 line in FIG. 20.
Figure 22:
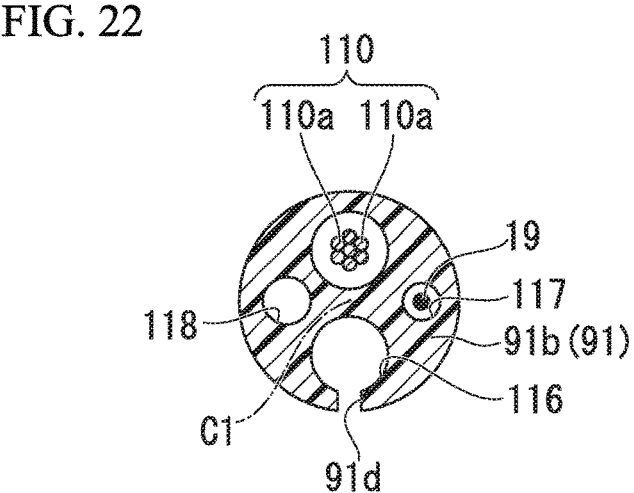
FIG. 22 is a view showing a cross section taken along A8-A8 line in FIG. 20.
Figure 23:
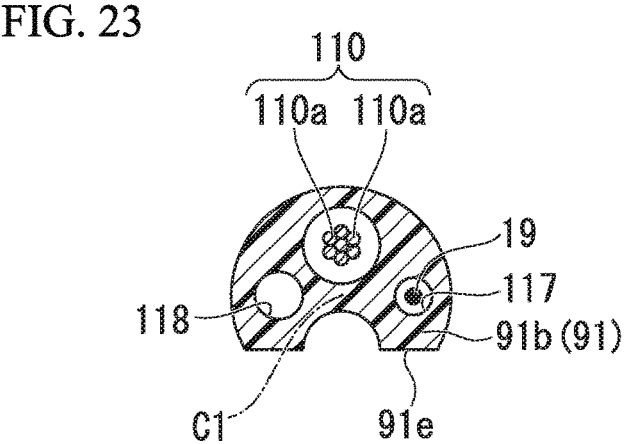
FIG. 23 is a view showing a cross section taken along A9-A9 line in FIG. 20.
Figure 24:
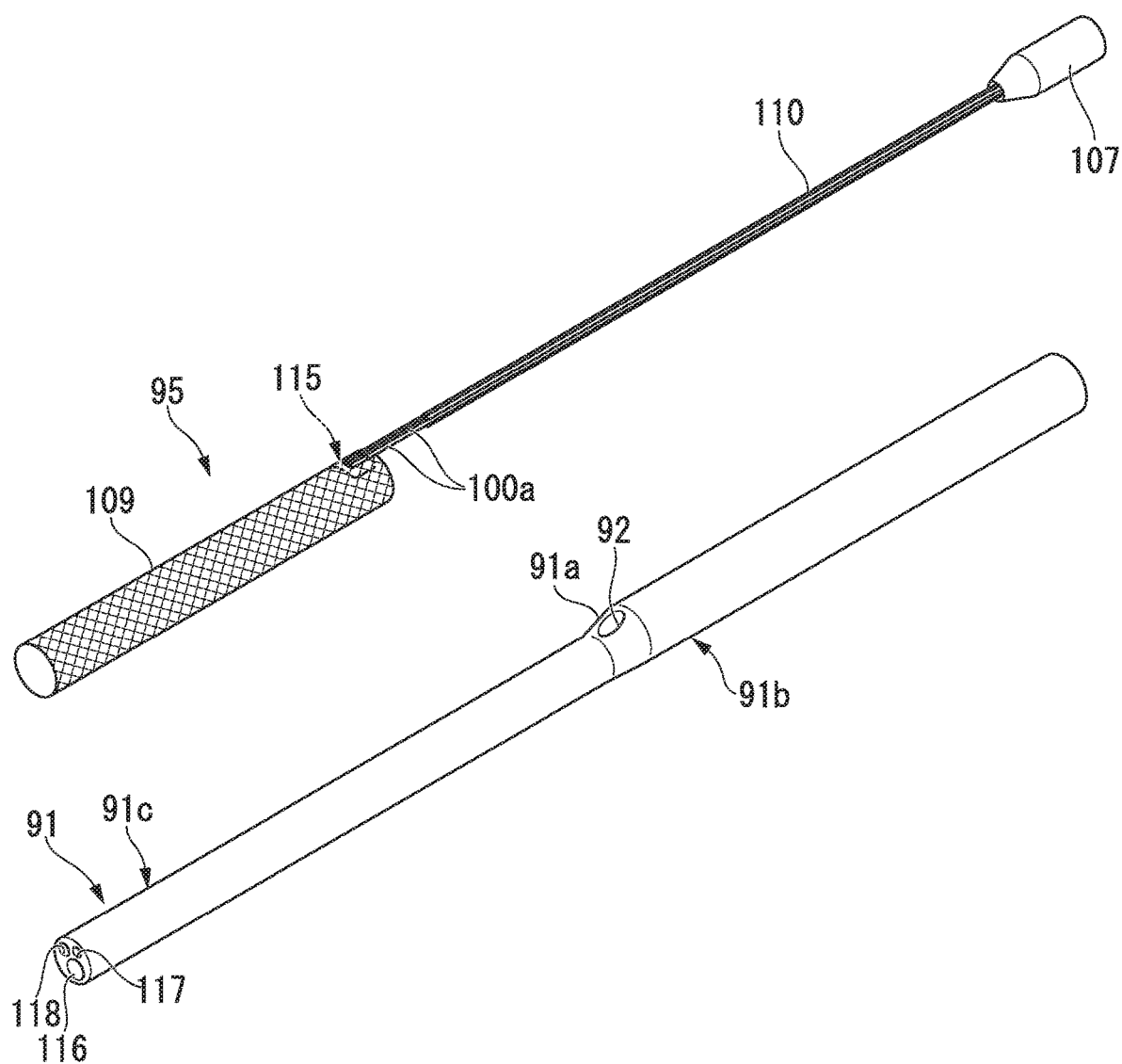
FIG. 24 is a perspective view showing a multi-lumen tube and a torque transmitting member which are disassembled used in the endoscopic treatment tool.
Figure 25:
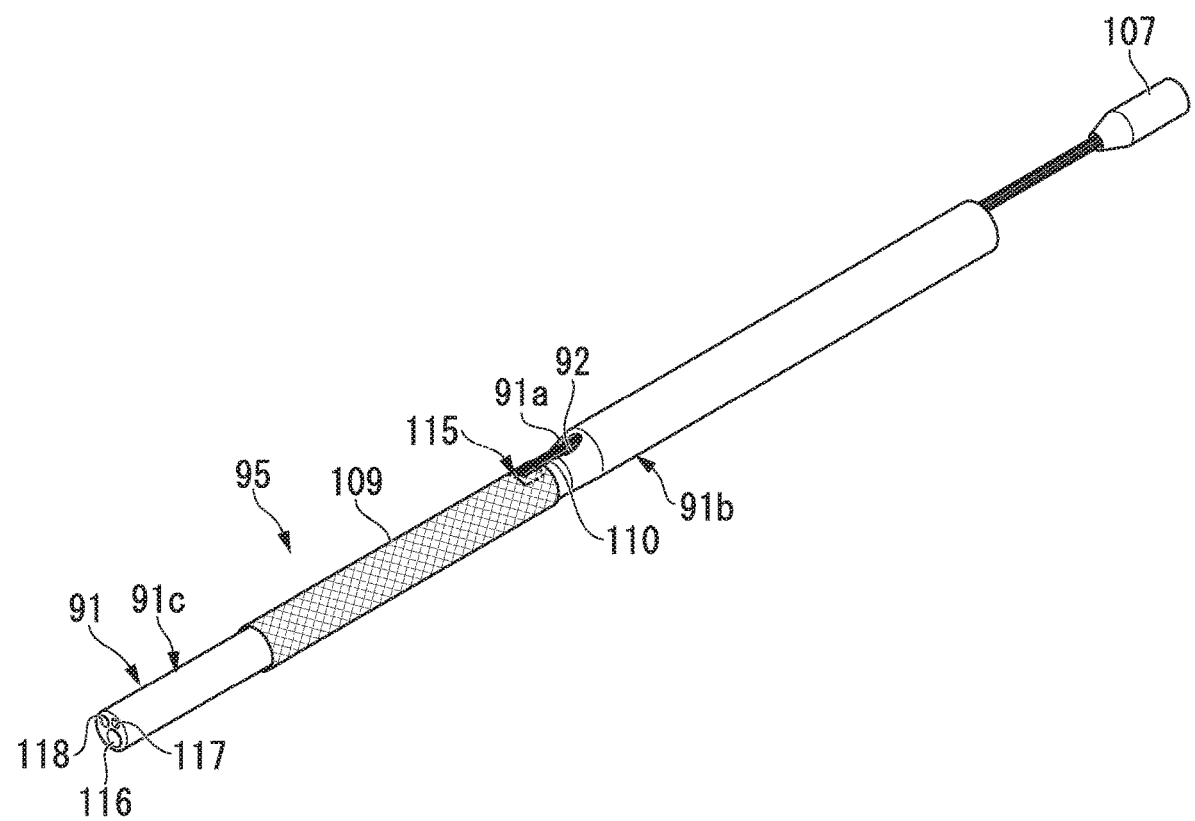
FIG. 25 is a perspective view showing a state of attaching the torque transmitting member to the multi-lumen tube.
Figure 26:
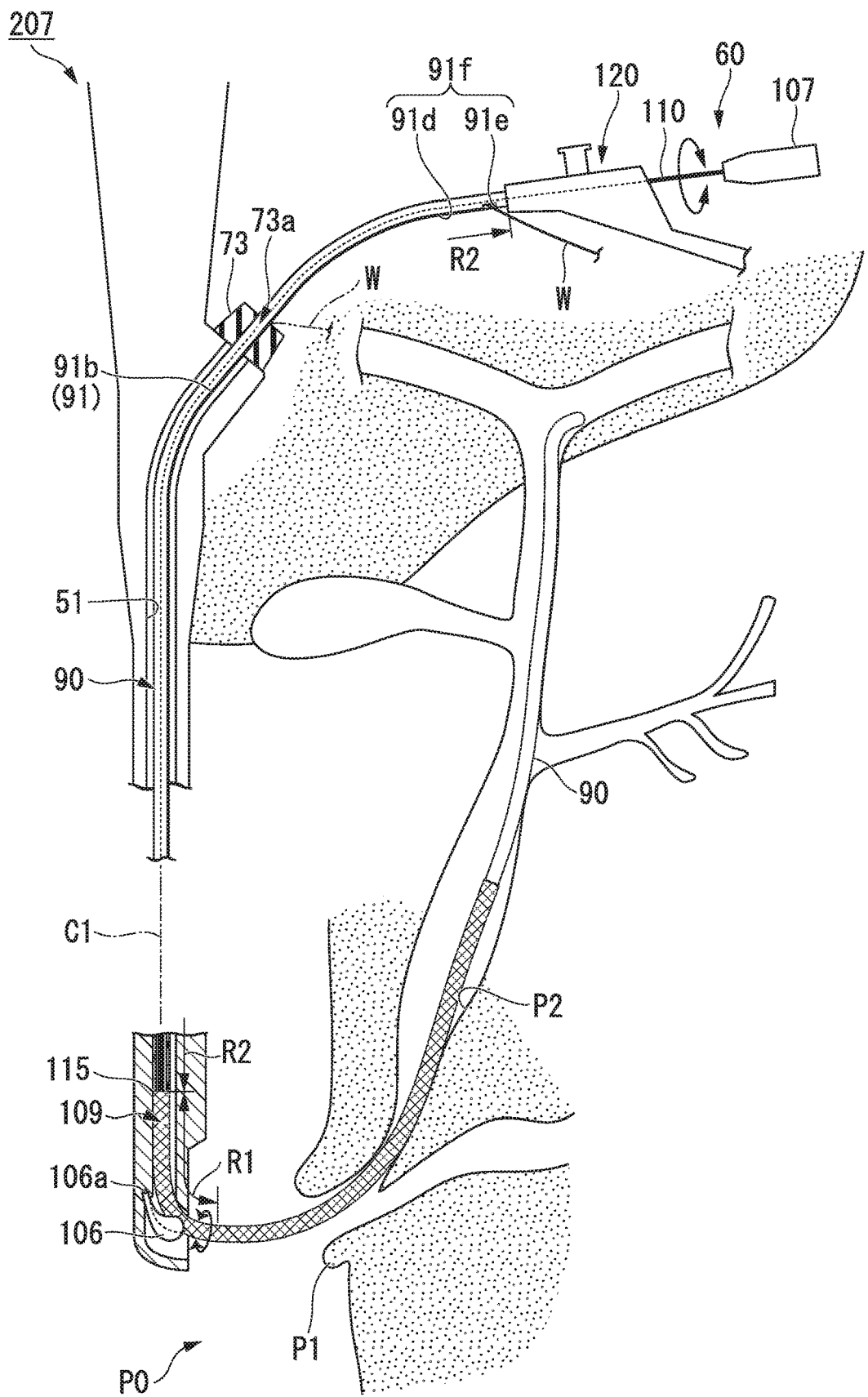
FIG. 26 is a view showing procedures using the endoscopic treatment tool.

Next, a second embodiment of the present invention will be described by referring to FIG. 20 to FIG. 26, however, elements same as that of the first embodiment will be affixed with the same reference signs of the first embodiment, and only the different configurations will be described. FIG. 20 is a side view showing a cross section of an endoscopic treatment tool according to a second embodiment of the present invention. FIG. 21 is a view showing a cross section taken along A7-A7 line in FIG. 20. FIG. 22 is a view showing a cross section taken along A8-A8 line in FIG. 20. FIG. 23 is a view showing a cross section taken along A9-A9 line in FIG. 20. FIG. 24 is a perspective view showing a multi-lumen tube and a torque transmitting member which are disassembled used in the endoscopic treatment tool. FIG. 25 is a perspective view showing a state of attaching the torque transmitting member to the multi-lumen tube. FIG. 26 is a view showing procedures using the endoscopic treatment tool.

As shown from FIG. 20 to FIG. 23, an endoscopic treatment tool 60 according to the present embodiment has a shaft 90, a treatment portion 113 disposed more distally than the shaft 90, and an operation portion 120 disposed at a proximal portion of the shaft 90 for operating the treatment portion 113.

The shaft 90 according to the present embodiment, as shown in FIG. 24 and FIG. 25, is a multi-lumen tube (elongated member) 91. In FIG. 24 and FIG. 25, a coating tube 111 of a torque transmitting member 95 described below is not shown.

As shown in FIG. 24, the multi-lumen tube 91 is formed have a proximal-end outer diameter larger than a distal-end outer diameter, and the multi-lumen tube 91 is configured to have a transition portion 91a formed at the boundary portion between the distal-end portion and the proximal-end portion. As shown in FIG. 21 to FIG. 23, at least three lumens 116, 117, 118 described above are formed over the entire length of the multi-lumen tube 91. Further, a torque lumen (lumen) 92 is formed from the proximal end to the transition portion 91a.

A tube main body 91b is defined as a portion more proximal than a middle portion of the distal end of the multi-lumen tube 91 and the transition portion 91a, and a knife support portion 91c is defined as a portion more distal than the tube main body 91b. As shown in FIG. 20 and FIG. 22, a narrow notch 91d is formed at the guidewire lumen 116 of the tube main body 91b, and the narrow notch 91d is configured to reach the outer circumferential surface of the tube main body 91b. The narrow notch 91d is formed over substantially the whole length of a shaft region R2 more proximal than the transition portion 91 that will be described below. A width of the narrow notch 91d is formed to be slightly smaller than an outer diameter of the guidewire W (see FIG. 26) used with the endoscopic treatment tool 60. A wide notch 91e having a width larger than the outer diameter of the guidewire W used with the endoscopic treatment tool 60 is formed at a proximal end of the narrow notch 91d.

Both the narrow notch 91e and the wide notch 91d are configured to form a notch 91f.

As shown from FIG. 20 to FIG. 25, the shaft 90 has the tube main body 91b and the torque transmitting member 95 disposed at the tube main body 91b.

As shown in FIG. 20, FIG. 24, and FIG. 25, the torque transmitting member 95 has a braid 109 formed from a metal material in a tubular shape, a wire 110 having a distal end portion fixed on an outer circumferential surface of the braid 109, and a coating tube 111 configured to coat the braid 109.

In the present embodiment, as shown in FIG. 21 and FIG. 24, the wire 110 is formed by arranging a plurality of strands 110a parallelly to the axis C1 and then fixing the plurality of strands 110a to each other by only welding distal ends and proximal ends of the plurality of stands 110a. The stand 110a can be formed from a stainless wire or a nickel-titanium alloy wire.

As shown in FIG. 20 and FIG. 25, a few strands 110a among the plurality of strands 110a are extended toward the distal end side and fixed to the outer circumferential surface of the proximal end portion of the braid 109 by welding. That is, the braid 109 and the wire 110 are fixed to each other by a welded portion (joining portion) 115. The welded portion 115 is sandwiched between the proximal end portion of the braid 109 and the proximal portion of the coating tube 111. The wire 110 may be formed from a single thick nickel-titanium alloy.

The proximal end portion of the wire 110 is fixed to a grip (rotation-torque input portion) 107 having a larger diameter than that of the wire 110.

The operation portion 120 is configured to be able to adjust the exposure amount of the knife portion 19a exposed outside the multi-lumen tube 91 in the region between the two through holes formed in the vicinity of the distal end of the multi-lumen tube 91.

As shown in FIG. 20, an opening 122 is formed at the proximal end of the operation portion main body 121 of the operation portion 120, and the torque lumen 92 is formed to communicate with the opening formed at the proximal end of the operation portion main body 121. The grip 107 is provided to protrude from the opening 122, and the grip 107 is configured to be able to input the rotation torque to the wire 110.

Configurations of the braid 109 and the coating tube 111 are the same with that of the braid 8 and the coating member 9 according to the first embodiment.

The knife support portion 91c, the braid 109, and the coating tube 111 are fixed by a flexible adhesive such that even if in a bent channel of the endoscope, it is still possible to bend the knife support portion 91c, the braid 109, and the coating tube 111 for transmitting the rotation torque easily, or the knife support portion 91c, the braid 109, and the coating tube 111 are configured by forming the coating tube 111 from a shrink tube having an inner diameter smaller than the outer diameter of the braid 109, and then flexibly and tightly adhering the coating tube 111 with the braid 109 such that the braid 109 is easy to bend due to the shrinking force of the coating tube 111.

The distal end side of the shaft 90 is a shaft region R1 at which the braid 109 and the coating tube 111 are attached to the outer circumferential surface of the knife support portion 91c. Meanwhile, at the proximal end side of the shaft 90, the wire 110 is not attached to the outer circumferential surface of the tube main body 91b, and the wire 110 is disposed inside the torque lumen 92 of the tube main body 91b so as to be freely rotatable. The proximal end side of the shaft 90 is the shaft region R2.

The part corresponding to the shaft region R2 of the multi-lumen tube 91 is formed from a material having a torque transmitting force less than that of the torque transmitting member 95. In other words, the part corresponding to the shaft region R2 is formed from a material easy to be twisted.

In the state in which the duodenal papilla is captured in the field of view of the imaging portion of the endoscope 100, when the shaft 90 is inserted into the duodenal papilla, it is necessary to largely bend the shaft 90 in a small curvature radius by the raising stand 106 of the endoscope 100. At this time, the shaft 90 bent by the raising stand 106 is largely bent in a smaller curvature radius than that of the channel 51 which is bent due to the bending of the insertion body 101 of the endoscope 100.

The material and the shape of the wire 110 can be set to enhance the torque transmissibility of the wire 110, however, the flexibility of the wire 110 is degraded. In the case when the flexibility of the wire 110 is degraded, it will be difficult to advance and retract the shaft 90 (the shaft region R2) following the raised raising stand 106. In this case, it is necessary to release the raised state of the raising stand 106, however, once the raised state of the raising stand 106 is released, the proximal indicator 12 cannot be captured in the field of view of the imaging portion of the endoscope 100.

According to the present embodiment, as shown in FIG. 26, when the proximal indicator 12 is positioned in the field of view of the imaging portion of the endoscope 100, in the channel 51, the welded portion 115 is set to be positioned more proximally than the proximal end 106a of the raising stand 106. That is, in the channel 51, the distal end of the wire 110 is set to be at a position more proximal than the proximal end 106a of the raising stand 106, and the region between the proximal end and the distal end of the braid 109 is raised by the raising stand 106. In other words, the shaft region R2 is set to be positioned more proximally than the proximal end 106a of the raising stand 106.

Accordingly, it is not necessary to release the raised state of the raising stand 106, and it is possible to maintain the state in which the proximal indicator 12 is captured in the field of view of the imaging portion of the endoscope 100 while maintaining the torque transmissibility to the braid 109.

The treatment portion 113 has the same configuration with that of the treatment portion 13 according to the first embodiment.

Same as the first embodiment described above, as shown in FIG. 20, the distal indicator 11 and the proximal indicator 12 are disposed on the outer circumferential surface of the braid 109. Details of the distal indicator 11 and the proximal indicator 12 are the same with the distal indicator 11 and the proximal indicator 12 according to the first embodiment, and the description will be omitted.

The endoscopic treatment tool 60 having such a configuration is combined with the endoscope 100 shown in FIG. 26 to configure an endoscopic system 207.

Procedures using the endoscopic treatment tool 60 will be described. The guidewire W is inserted into the channel 51 through the through hole 73a of the forceps port 73 of the endoscope 100. The portion of the shaft 90 where the narrow notch 91d is formed is inserted into the forceps port 73, and the wide notch 91e is positioned more proximally than the forceps port 73. This guidewire W is guided into the bile duct P2 via the duodenum P0.

The proximal end portion of the guidewire W is inserted into the distal end of the guidewire lumen 116 of the endoscopic treatment tool 60, and the guidewire W is drawn out from the wide notch 91e of the shaft 90. The shaft 90 of the endoscopic treatment tool 60 is inserted into the channel 51 through the through hole 73a of the forceps port 73. When the shaft 90 is inserted into the forceps port 73, a friction force generated between the valve of the forceps port 73 and the outer circumferential surface of the shaft 90 applies such that the forceps port 73 and the shaft 90 are almost water-tightly engaged with each other.

The user adjusts the insertion amount of the shaft 90 inserted into the channel 51 of the endoscope 100, and cause the endoscopic treatment tool 60 into a direction adjusting state in which the treatment portion 113 is protruded from the channel 51. At this time, the shaft region R2 of the shaft 90, that is, the tube main body 91b is inserted into the forceps port 73. The friction force is applying between the forceps port 73 and the outer circumferential surface of the tube main body 91b in the shaft region R2.

Once the operator grasps the grip 107 and inputs the rotation about the axis C1, the rotation torque is transmitted to the braid 109 and the coating tube 111 via the wire 110 inserted into the torque lumen 92 of the tube main body 91b, and thus transmitted to the shaft region R1. At this time, since the distal end of the shaft region R2 is connected to the proximal end side of the shaft region R1 via the transition portion 91a, the rotation torque is also transmitted to the shaft region R2 from the shaft region R1. However, since the multi-lumen tube 91 is formed by the material having a lower torque transmissibility than that of the torque transmitting member 95 and is easy to be twisted, the rotation torque applied to the distal end of the shaft region R2 is absorbed due to the torsion of the multi-lumen tube 91. Accordingly, the rotation torque is not transmitted to the operation portion main body 121 and it is not necessary to rotate the operation portion main body 121 about the axis C1 at hand.

Since the wire 110 is inserted into the torque lumen 92, the rotation torque transmitted from the grip 107 is barely affected by the friction force of the forceps port 73.

The notch 91f is formed at the guidewire lumen 116 of the tube main body 91b in the shaft region R2. Accordingly, it is easy to perform the procedures of pulling out the guidewire W inserted into the guidewire lumen 116 from the notch 91f to the outside and inserting the shaft 90 along the guidewire W.

The narrow notch 91d is formed to have a width slightly smaller than the outer diameter of the guidewire W. The multi-lumen tube 91 is formed from a resin material so as to be elastically deformable, therefore the guidewire W can be pulled out through the narrow notch 91d by causing the multi-lumen tube 91 to be elastically deformed.

In a case of initiating the procedures only using the endoscopic treatment tool 60 and inserting the guidewire through the guidewire lumen on the occasion of the procedures, since the narrow notch 91d is smaller than the outer diameter of the guidewire W, the guidewire W will not slip out from the narrow notch 91d in the middle portion of the narrow notch 91d, and the guidewire W can be inserted until the distal end of the endoscopic treatment tool 60 is reached.

In the present embodiment, the same effect can be achieved as that of the first embodiment.

Further, in the present embodiment, as same as the first embodiment, a pre-curved shape portion can be provided.

In a case when the pre-curved portion is provided in the vicinity of the distal end of the multi-lumen tube 91, the braid 109 is positioned at a side closer to the proximal end of the multi-lumen tube 91 than the proximal end of the pre-curved shape portion, and the braid 109 is fixed to the distal end of the wire 110 and the multi-lumen tube 91.

The first embodiment and the second embodiment of the invention have been described above with reference to the drawings, but specific structures of the invention are not limited to the embodiments and may include various modifications without departing from the scope of the invention. Furthermore, it is clear that the configuration according to each embodiment can be suitably combined to be adopted.

The present invention is not limited by the foregoing description, but is only limited by the scope of the appended claims.

What is claimed is:

1. A method of inserting an endoscopic treatment tool into a bile duct, the method comprising:
   inserting an elongated member of the endoscopic treatment tool into a channel of an endoscope such that a distal end of the elongated member protrudes from a distal opening of the channel;
   inserting the distal end of the elongated member into a duodenal papilla;
   bringing the distal end of the elongated member to a branching region of a common bile duct and a cystic duct;
   recognizing an orientation of the distal end of the elongated member by observing a distal indicator disposed on the elongated member which is protruded from the duodenal papilla into a duodenum, when the distal end of the elongated member reaches the branching region of the common bile duct and the cystic duct;
   advancing the elongated member toward intrahepatic bile ducts; and
   recognizing the orientation of the distal end of the elongated member by observing a proximal indicator disposed on the elongated member which is protruded from the duodenal papilla into the duodenum, when the distal end of the elongated member reaches a branching region of a left hepatic duct and a right hepatic duct.

2. The method according to claim 1, wherein each of the distal indicator and the proximal indicator has a width that is less than half of a circumferential dimension of an outer circumferential surface of the elongated member in a circumferential direction of the elongated member, respectively.

3. The method according to claim 1, wherein:
   the distal indicator is disposed between a position of 5 centimeters from the distal end of the elongated member toward a proximal end side of the elongated member and a position of 10 centimeters from the distal end of the elongated member toward the proximal end side of the elongated member, and the proximal indicator is disposed between a position of 10 centimeters from the distal end of the elongated member toward the proximal end side of the elongated member and a position of 15 centimeters from the distal end of the elongated member toward the proximal end side of the elongated member.

4. The method according to claim 1, wherein:
the distal indicator includes a first distal indicator and a second distal indicator, and
the first distal indicator and the second distal indicator are disposed at opposite sides in a radial direction of the elongated member.

5. The method according to claim 4, wherein a color of the first distal indicator and a color of the second distal indicator are formed by a colored paint.

6. The method according to claim 5, wherein the color of the first distal indicator is different from the color of the second distal indicator.

7. The method according to claim 1, wherein:
the proximal indicator includes a first proximal indicator and a second proximal indicator, and
the first proximal indicator and the second proximal indicator are disposed at opposite sides in a radial direction of the elongated member.

8. The method according to claim 7, wherein a color of the first proximal indicator and a color of the second proximal indicator are formed by a colored paint.

9. The method according to claim 8, wherein the color of the first proximal indicator is different from the color of the second proximal indicator.

10. The method according to claim 1, wherein:
the endoscope includes a raising stand for raising the treatment tool inserted into the channel, and
in a state in which the proximal indicator is positioned in a field of view of an observation optical system of the endoscope, a proximal end of a braid of the endoscopic treatment tool is positioned on a proximal side of a proximal end of the raising stand along a longitudinal direction of the elongated member.

11. The method according to claim 1, wherein:
the elongated member includes a pre-curved shape portion disposed between a distal end of the distal indicator and the distal end of the elongated member, the pre-curved shape portion having a restoring force so as to restore to a curved shape in which a longitudinal axis of the elongated member is curved, and
the distal end of the distal indicator is disposed in a vicinity of a proximal end of the pre-curved shape portion.

12. The method according to claim 1, wherein:
a distal portion of the elongated member includes a pre-curved shape portion configured to restore to a curved shape, and
a distal end of the pre-curved shape portion is positioned in a range of a width of the distal indicator and the proximal indicator when viewed in a front view from a direction along a longitudinal axis of the elongated member.

13. The method according to claim 1, wherein the elongated member includes a braid extending from a proximal end to a distal end, the proximal end of the braid being more proximal than the proximal indicator, and the distal end of the braid being more distal than the distal indicator.

* * * * *